(12) United States Patent
Ostresh et al.

(10) Patent No.: US 6,359,144 B1
(45) Date of Patent: Mar. 19, 2002

(54) COMBINATORIAL LIBRARIES OF BICYCLIC GUANIDINE DERIVATIVES AND COMPOUNDS THEREIN

(75) Inventors: John M. Ostresh, Encinitas, CA (US); Jean-Philippe Meyer, Holland, PA (US); Colette T. Dooley, San Diego, CA (US); Sylvie E. Blondelle, San Diego, CA (US); Christa C. Schoner, San Diego, CA (US); Richard A. Houghten, Del Mar, CA (US)

(73) Assignee: Lion Bioscience AG (DE)

( * ) Notice: Subject to any disclaimer, the term of this patent is extended or adjusted under 35 U.S.C. 154(b) by 0 days.

(21) Appl. No.: 09/018,173

(22) Filed: Feb. 3, 1998

Related U.S. Application Data

(60) Provisional application No. 60/104,594, filed on Feb. 4, 1997.

(51) Int. Cl.$^7$ ............... C07D 403/02; C07D 249/00; A61K 31/4188
(52) U.S. Cl. ................... 548/303.1; 514/393
(58) Field of Search ............... 514/393; 548/303.1

(56) References Cited

U.S. PATENT DOCUMENTS

| | | | | |
|---|---|---|---|---|
| 2,782,205 A | * | 2/1957 | McKay et al. | 548/303.1 |
| 3,865,836 A | * | 2/1975 | Van Gelder et al. | 548/303.1 |
| 4,328,330 A | | 5/1982 | Wellner et al. | 528/45 |

FOREIGN PATENT DOCUMENTS

| | | |
|---|---|---|
| DE | 3018023 A1 | 12/1981 |

OTHER PUBLICATIONS

Bajusz, et al, "Further Enhancement of Analgesic Activity: Enkephalin Analogs With Terminal Guanidino Group," *FEBS Letters*, 110(1):85–87 (1980).
Corey and Ohtani, *Tetrahedron Letters*, 30:5227–5230 (1989).
Esser et al., "Cyclic guanidines: III. Synthesis of Novel 8,13,15 Triazasteroids and related heterocycles," *Synthesis* 72–78 (1990).
Esser et al., "Cyclic guanidines: V. Synthesis of Novel Benzodiazepines and related systems by intramolecular electrophilic aromatic substitution." *Synthesis* 77–82 (1994).
Gordon et al., "Applications of combinatorial technologies to drug discovery. 2. Combinatorial organic synthesis, library screening strategies, and future directions," *J. of Med. Chem.*, 37 (10):1386–1401 (1994).
Gallop et al., "Applications of combinatorial technologies to drug discovery. 1. Background and peptide combinatorial libraries," *J. of Med. Chem.*, 37(9):1233–1251 (1994).
Houghten et al., "Generation and use of synthetic peptide combinatorial libraries for basic research and drug discovery," *Nature*, 354:84–86 (1991).
Kosasayama & Ishikawa, "Cyclic guanidines. VII. Structure–activity relationships of hypoglycemic cyclic guanidines," *Chem. Pharm. Bull.* 27(7): 1596–1603 (1979).
Nagarajan et al., *Synthetic Communications*, 22(8):1191–1198 (1992).
Ostresh et al., "Libraries from libraries: Chemical transformation of combinatorial libraries to extend the range and repertoire of chemical diversity," *Proc. Natl. Acad. Sci. USA* 9:11138–11142 (1994).
Ostresh et al., "Peptide Libraries: Determination of Relative Reaction Rates of Protected Amino Acids in Competitive Couplings," *Biopolymers,* 84:1661–1689 (1994).
Pinilla et al., "Rapid Identification of High Affinity Peptide Ligands Using Positional Scanning Synthetic Peptide Combinatorial Libraries," *BioTecniques,* 13(6):901–905 (1992).

* cited by examiner

*Primary Examiner*—Floyd D. Higel
(74) *Attorney, Agent, or Firm*—Law Offices of David Spolter; David Spolter

(57) ABSTRACT

The invention provides a rapid approach for combinatorial synthesis and screening of combinatorial libraries of bicyclic guanidine compounds. The present invention further provides the compounds made by the combinatorial synthesis and individually as well as methods of using the same.

11 Claims, 6 Drawing Sheets

COMBINATORIAL LIBRARIES OF BICYCLIC GUANIDINE DERIVATIVES AND COMPOUNDS THEREIN

This application claims the benefit of U.S. Provisional Application No. 60/104,594, which was converted from U.S. Ser. No. 08/794,070, filed Feb. 4, 1997.

BACKGROUND OF THE INVENTION

1. Field of the Invention

The present invention relates generally to the combinatorial synthesis of bicyclic guanidine derivatives. More specifically, the invention provides novel bicyclic guanidines as well as novel combinatorial libraries comprised of many such compounds, and methods of synthesizing the libraries.

2. Background Information

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as the bicyclic guanidine compounds of the present invention.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, by Dooley in U.S. Pat. No. 5,367,053, Huebner in U.S. Pat. No. 5,182,366, Appel et al. in WO PCT 92/09300, Geysen in published European Patent Application 0 138 855 and Pirrung in U.S. Pat. No. 5,143,854. Such SCLs provide the efficient synthesis of an extraordinary number of various peptides in such combinatorial libraries and the rapid screening of the library which identifies lead pharmaceutical peptides.

Peptides have been, and remain, attractive targets for drug discovery. Their high affinities and specificities toward biological receptors as well as the ease with which large peptide libraries can be combinatorially synthesized make them attractive drug targets. The screening of peptide combinatorial libraries has led to the identification of many biologically-active lead compounds. However, the therapeutic application of peptides is limited by their poor stability and bioavailability in vivo. Therefore, there is a need to synthesize and screen compounds which can maintain high affinity and specificity toward biological receptors but which have improved pharmacological properties relative to peptides.

Combinatorial approaches have recently been extended to "organic," or non-peptide, libraries. The organic libraries, however, are of limited diversity and generally relate to peptidomimetic compounds; in other words, organic molecules that retain peptide chain pharmacophore groups similar to those present in the corresponding peptide. Although the present invention is principally derived from the synthesis of dipeptides, the dipeptides are substantially modified. In short, they are chemically modified through acylation, reduction, and cyclization into the subject bicyclic guanidines, thus providing mixtures and individual compounds of substantial diversity.

Significantly, many biologically active compounds contain guanidine functionalities. Guanidine-containing compounds have been reported to be useful as having hypotensive and adrenergic blocking effects as described, for example, in E. J. Corey and Mitsuaki Ohtani, *Tetrahedron Letters.*, 30(39):5227–5230 (1989). Guanidine-containing compounds also can be used as sweeteners as described, for instance, in Nagarajan et al. *Synthetic Communications.*, 22(8):1191–1198 (1992). Because guanidine moieties are found in many biologically active compounds and are known to have useful therapeutic implications, there is a need to further study and develop large numbers of bicyclic guanidines and their binding to biological receptors.

This invention satisfies these needs and provides related advantages as well. The present invention overcomes the known limitations to classical organic synthesis of guanidine-containing compounds as well as the shortcomings of combinatorial chemistry with small organics or peptidomimetics. Moreover, the present invention provides a large array of diverse bicyclic guanidines which can be screened for biological activity, and as described below, are biologically active.

SUMMARY OF THE INVENTION

The invention provides a rapid approach for combinatorial synthesis and screening of combinatorial libraries of bicyclic guanidine compounds. The present invention further provides individual compounds contained within the combinatorial library and methods of using the same, such as for effecting analgesia. More specifically, the present invention relates to the generation of synthetic combinatorial libraries and of organic compounds based on the formula:

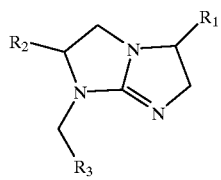

or the formula:

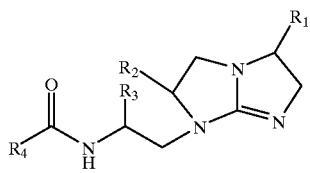

wherein $R^1$, $R^2$, $R^3$ and $R^4$ have the meanings provided below.

DETAILED DESCRIPTION OF THE INVENTION

Figure 1:
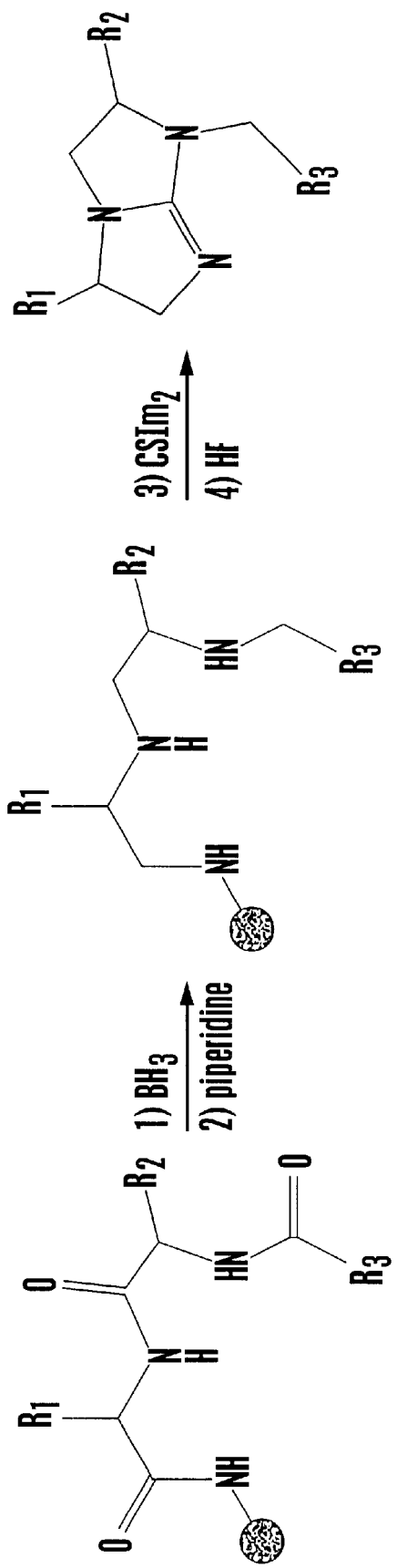
FIG. 1 shows the Reaction Scheme I for preparing combinatorial libraries and compounds of the present invention.

The present invention relates to the generation of synthetic combinatorial libraries and individual compounds which are based on the Formula I:

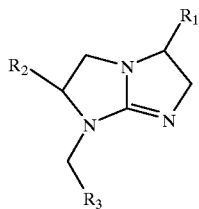

FORMULA I

In the above Formula I:

$R^1$ is a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkenyl, $C_3$ to $C_7$ substituted cycloalkenyl, benzyl, or substituted benzyl;

$R^2$ is a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, substituted benzyl, naphthyl, or substituted naphthyl; and $R^3$ is a hydrogen atom, $C_1$ to $C_{10}$ alkyl, $C_2$ to $C_{10}$ alkenyl, $C_1$ to $C_{10}$ substituted alkyl, $C_2$ to $C_{10}$ alkynyl, $C_3$ to $C_7$ substituted cycloalkyl, $C_3$ to $C_7$ cycloalkenyl, $C_3$ to $C_7$ substituted cycloalkenyl, $C_7$ to $C_{16}$ phenylalkyl, $C_7$ to $C_{16}$ substituted phenylalkyl, $C_7$ to $C_{16}$ phenylalkenyl or $C_7$ to $C_{16}$ substituted phenylalkenyl.

If desired, any one, any two or all three of the above R groups can contain any of the above-described substituents except for a hydrogen atom.

In one embodiment of the above bicyclic guanidine combinatorial libraries and compounds, the substituents in Formula I are as follows:

$R^1$ is methyl, benzyl, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, dimethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, 4-iodobenzyl, or 4-methoxybenzyl;

$R^2$ is methyl, benzyl, hydrogen, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, hydroxyethyl, 4-iodobenzyl, or 4-methoxybenzyl; and $R^3$ is 3-phenylbutyl, m-toluylethyl, 3-fluorophenylethyl, p-toluylethyl, 4-fluorophenylethyl, 3-methoxyphenylethyl, 4-methoxyphenylethyl, 4-ethoxyphenylethyl, 3-(3,4-dimethoxyphenyl)propyl, 4-biphenylethyl, 3,4-dimethoxyphenylethyl, phenylethyl, 3-phenylpropyl, 4-phenylbutyl, butyl, heptyl, isobutyryl, (+/−)-2-methylbutyl, isovaleryl, 3-methylvaleryl, 4-methylvaleryl, (tert-butyl)ethyl, cyclohexylmethyl, cyclohexylethyl, cyclohexylbutyl, cycloheptylmethyl, 2-hydroxypropyl, ethyl, cyclobutylmethyl, cyclopentylmethyl, 3-cyclopentylpropyl, cyclohexylpropyl, 4-methyl-1-cyclohexylmethyl, 4-(tert-butyl)-1-cyclohexylmethyl, 2-norbornylethyl, 1-adamantylethyl, 2-ethylbutyl, 3,3-diphenylpropyl, 2-methyl-4-nitro-1-imidazolylpropyl, cyclopentylethyl, or 3-indolylethyl.

A further embodiment of the subject invention provides a combinatorial library and individual compounds shown to have significant biological activity, which compounds, individually or contained within the combinatorial library, have the following substituents in Formula I:

$R^1$ is methyl or cyclohexyl;

$R^2$ is 4-methoxybenzyl, 2-methylpropyl or cyclohexyl; and $R^3$ is 3-cyclohexylpropyl or 1-adamantylethyl.

More specifically, the individual compounds are wherein (1) $R^1$ is methyl, $R^2$ is 4-methoxybenzyl, and $R^3$ is 3-cyclohexylpropyl; (2) $R^1$ is methyl, $R^2$ is 4-methoxybenzyl, and $R^3$ is 1-adamantylethyl; (3) $R^1$ is cyclohexyl, $R^2$ is 4-methoxybenzyl, and $R^3$ is 1-adamantylethyl; (4) $R^1$ is cyclohexyl, $R^2$ is 4-methoxybenzyl, and $R^3$ is 3-cyclohexylpropyl; (5) $R^1$ is cyclohexyl, $R^2$ is 2-methylpropyl, and $R^3$ is 1-adamantylethyl; (6) $R^1$ is cyclohexyl, $R^2$ is cyclohexyl, and $R^3$ is 1-adamantylethyl; (7) $R^1$ is cyclohexyl, $R^2$ is 2-methylpropyl, and $R^3$ is 3-cyclohexylpropyl; (8) $R^1$ is methyl, $R^2$ is cyclohexyl, and $R^3$ is 1-adamantylethyl; (9) $R^1$ is methyl, $R^2$ is cyclohexyl, and $R^3$ is 3-cyclohexylpropyl; (10) $R^1$ is methyl, $R^2$ is methylpropyl, and $R^3$ is 1-adamantylethyl; (11) $R^1$ is cyclohexyl, $R^2$ is cyclohexyl and $R^3$ is 3-cyclohexylpropyl; and (12) $R^1$ is methyl, $R^2$ is methylpropyl, and $R^3$ is 3-cyclohexylpropyl. The amino acids from which these individual compounds were derived, as well as the individual compounds described below, can be in the L- or D-configuration, resulting in the same R group, varying only in its stereochemistry. Therefore, in the above compounds and the ones below, the R groups can be in either the R or S configuration, or a mixture of the two.

Additional individual compounds of the subject invention shown to have significant biological activity include those having the following substituents in Formula I:

$R^1$ is benzyl or butyl;

R² is 2-naphthylmethyl, 4-ethoxybenzyl, cyclohexylmethyl, 4-chlorobenzyl, 4-iodobenzyl, 4-methoxybenzyl, 4-nitrobenzyl, benzyl, cyclohexyl, N-ethyl,N-thiocarbonylimidazole-aminobutyl, or 4-fluorobenzyl; and R³ is methyl, (tert-butyl)ethyl or isovaleryl.

More preferably, seventeen individual compounds shown to have significant biological activity are wherein (1) R¹ is benzyl, R² is 2-naphthylmethyl, R³ is methyl; (2) R¹ is benzyl, R² is 4-ethoxybenzyl, R³ is methyl; (3) R¹ is benzyl, R² is 2-naphthylmethyl, R³ is methyl; (4) R¹ is benzyl, R² is cyclohexylmethyl, R³ is methyl; (5) R¹ is benzyl, R² is 4-chlorobenzyl, R³ is methyl; (6) R¹ is benzyl, R² is 4-ethoxybenzyl, R³ is methyl; (7) R¹ is benzyl, R² is 4-iodobenzyl, R³ is methyl; (8) R¹ is benzyl, R² is 4-methoxybenzyl, R³ is methyl; (9) R¹ is benzyl, R² is 4-nitrobenzyl, R³ is methyl; (10) R¹ is benzyl, R² is benzyl, R³ is (tert-butyl)ethyl; (11) R¹ is benzyl, R² is cyclohexyl, R³ is methyl; (12) R¹ is benzyl, R² is 4-chlorobenzyl, R³ is methyl; (13) R¹ is benzyl, R² is benzyl, R³ is isovaleryl; (14) R¹ is benzyl, R² is N-ethyl,N-thiocarbonylimidazole-aminobutyl, R³ is methyl; (15) R¹ is butyl, R² is benzyl, and R³ is methyl; (16) R¹ is benzyl, R² is 4-fluorobenzyl, R³ is methyl; (17) R¹ is benzyl, R² is 4-fluorobenzyl, R³ is methyl.

Another embodiment of the subject invention provides a combinatorial library and individual compounds shown to have significant biological activity, which compounds, individually or contained within a combinatorial library, have the following substituents in Formula I:

R¹ is cyclohexyl or cyclohexylmethyl;

R² is cyclohexyl or cyclohexylmethyl; and

R³ is 4-(tert-butyl)-1-cyclohexylmethyl or 1-adamantylethyl.

More specifically, the individual compounds are wherein (1) R¹ is cyclohexyl, R² is cyclohexyl and R³ is 4-(tert-butyl)-1-cyclohexylmethyl; (2) R¹ is cyclohexyl, R² is cyclohexylmethyl and R³ is 4-(tert-butyl)-1-cyclohexylmethyl; (3) R¹ is cyclohexyl, R² is cyclohexylmethyl and R³ is 1-adamantylethyl; (4) R¹ is cyclohexyl, R² is cyclohexyl and R³ is 1-adamantylethyl; (5) R¹ is cyclohexylmethyl, R² is cyclohexyl and R³ is 4-(tert-butyl)-1-cyclohexylmethyl; (6) R¹ is cyclohexylmethyl, R² is cyclohexylmethyl and R³ is 4-(tert-butyl)-1-cyclohexylmethyl; (7) R¹ is cyclohexylmethyl, R² is cyclohexylmethyl and R³ is 1-adamantylethyl; and (8) R¹ is cyclohexylmethyl, R² is cyclohexyl and R³ is 1-adamantylethyl.

A further embodiment of the subject invention provides a combinatorial library and individual compounds shown to have significant biological activity, which compounds, individually or contained within a combinatorial library, have the following substituents in Formula I:

R¹ is cyclohexyl, cyclohexylmethyl, methyl, benzyl or methylsulfinylethyl;

R² is cyclohexyl, cyclohexylmethyl, benzyl, hydroxyethyl, 4-methoxybenzyl or 2-methylpropyl; and R³ is 4-(tert-butyl)-1-cyclohexylmethyl, 1-adamantylethyl, cyclohexylbutyl, ethyl and 4-biphenylethyl.

More preferably, twenty-one individual compounds shown to have significant biological activity are wherein (1) R¹ is cyclohexylmethyl, R² is cyclohexylmethyl and R³ is 4-(tert-butyl)-1-cyclohexylmethyl; (2) R¹ is cyclohexylmethyl, R² is cyclohexylmethyl and R³ is 1-adamantylethyl; (3) R¹ is cyclohexyl, R² is cyclohexylmethyl and R³ is 4-(tert-butyl)-1-cyclohexylmethyl; (4) R¹ is cyclohexyl, R² is cyclohexylmethyl and R³ is 1-adamantylethyl; (5) R¹ is cyclohexylmethyl, R² is cyclohexyl and R³ is 1-adamantylethyl; (6) R¹ is cyclohexylmethyl, R² is cyclohexyl and R³ is 4-(tert-butyl)-1-cyclohexylmethyl; (7) R¹ is cyclohexyl, R² is cyclohexyl and R³ is 4-(tert-butyl)-1-cyclohexylmethyl; (8) R¹ is cyclohexyl, R² is cyclohexyl and R³ is 1-adamantylethyl; and (9) R¹ is benzyl, R² is hydroxyethyl and R³ is ethyl; (10) R¹ is cyclohexyl, R² is 4-methoxybenzyl and R³ is cyclohexylbutyl; (11) R¹ is cyclohexyl, R² is 4-methoxybenzyl and R³ is 1-adamantylethyl; (12) R¹ is cyclohexyl, R² is 4-methoxybenzyl and R³ is cyclohexylbutyl; (13) R¹ is cyclohexyl, R² is cyclohexylmethyl and R³ is cyclohexylbutyl; (14) R¹ is benzyl, R² is benzyl and R³ is 4-biphenylethyl; (15) R¹ is cyclohexyl, R² is 2-methylpropyl and R³ is 1-adamantylethyl; (16) R¹ is benzyl, R² is benzyl and R³ is 1-adamantylethyl; (17) R¹ is benzyl, R² is benzyl and R³ is cyclohexylbutyl; (18) R¹ is cyclohexyl, R² is 2-methylpropyl and R³ is cyclohexylbutyl; (19) R¹ is benzyl, R² is benzyl and R³ is 4-(tert-butyl)-1-cyclohexylmethyl; (20) R¹ is methyl, R² is benzyl and R³ is ethyl; and (21) R¹ is methylsulfinylethyl, R² is benzyl and R³ is ethyl.

Additional individual compounds shown to have significant biological activity include those having the following substituents in Formula I:

R¹ is benzyl or N-(methyl)indol-3-ylmethyl;

R² is benzyl or indol-3-ylmethyl; and

R³ is 2,4 dinitrobenzyl or ethyl.

More preferably, three individual compounds shown to have significant biological activity are wherein (1) R¹ is benzyl, R² is benzyl and R³ is 2,4 dinitrobenzyl; (2) R¹ is benzyl, R² is indol-3-ylmethyl and R³ is ethyl; (3) R¹ is N-(methyl)indol-3-ylmethyl, R² is benzyl and R³ is ethyl.

The present invention also relates to the generation of synthetic combinatorial libraries and individual compounds which are based on the Formula II:

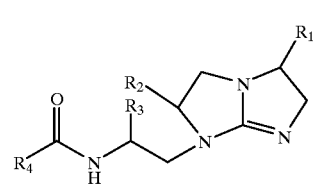

FORMULA II

In the above Formula II:

R¹ is a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, or substituted benzyl;

R² is a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, or substituted benzyl;

R³ is a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, or substituted benzyl; and R⁴ is a hydrogen atom, $C_1$ to $C_{10}$ alkyl, $C_2$ to $C_{10}$ alkenyl, $C_1$ to $C_{10}$ substituted alkyl, $C_2$ to $C_{10}$ alkynyl, $C_3$ to $C_7$ substituted cycloalkyl, $C_3$ to $C_7$ cycloalkenyl, $C_3$ to $C_7$ substituted cycloalkenyl, $C_7$ to $C_{16}$ phenylalkyl, $C_7$ to $C_{16}$ substituted phenylalkyl, $C_7$ to $C_{16}$ phenylalkenyl or $C_7$ to $C_{16}$ substituted phenylalkenyl.

If desired, any one, any two, any three or all four of the above R groups can contain any of the above-described substituents except for a hydrogen atom.

In one embodiment of the above bicyclic guanidine combinatorial libraries and compounds, the substituents in Formula II are as follows:

$R^1$ is methyl, benzyl, 2-butyl, 2-methylpropyl, 2-propyl, 2-bromobenzyloxycarbonylbenzyl, ethyl, dimethyl, propyl, butyl, 2-napthylmethyl, cyclohexylmethyl, 4-fluorobenzyl, 4-chlorobenzyl, cyclohexyl, 4-ethoxybenzyl, 4-iodobenzyl, or 4-methoxybenzyl;

$R^2$ is methyl, benzyl, 2-butyl, 2-methylpropyl, 2-propyl, 2-bromobenzyloxycarbonylbenzyl, ethyl, propyl, butyl, 2-naphthylmethyl, methylsulfonylethyl, cyclohexylmethyl, 4-fluorobenzyl, 4-chlorobenzyl, cyclohexyl, 4-ethoxybenzyl, 4-iodobenzyl, or 4-methoxybenzyl;

$R^3$ is methyl, benzyl, hydrogen, 2-methylpropyl, propyl, butyl, cyclohexylmethyl, 4-ethoxybenzyl, or 4-methoxybenzyl; and $R^4$ is 1-phenyl-1-cyclopropyl, 1-phenylpropyl, 2-phenylpropyl, m-xylyl, 3-fluorobenzyl, 3-bromobenzyl, 3-trifluoromethylbenzyl, p-xylyl, 3-methoxybenzyl, 4-bromobenzyl, 4-methoxybenzyl, 4-ethoxybenzyl, 1-(4-isobutylphenyl)ethyl, 3,4-dichlorobenzyl, 3-(3,4-dimethoxy)ethyl, 4-biphenylmethyl, 1-phenylpropen-2-yl, 2-trifluoromethylstryl, 3,4-dimethoxybenzyl, 3,4-dihydroxybenzyl, 2-methoxystyryl, phenyl, 4-chlorostyryl, 3-methoxyphenyl, 4-isopropylphenyl, 4-vinylphenyl, 4-fluorophenyl, 4-bromophenyl, 3,4-dimethoxystyryl, trans-styryl, 3,4-dimethylphenyl, 3-fluoro-4-methylphenyl, 3-bromo-4-methylphenyl, 3-iodo-4-methylphenyl, 3,4-dichlorophenyl, 4-biphenyl, 3,4-difluorophenyl, m-tolyl, benzyl, phenethyl, 3-methoxy-4-methylphenyl, 3-phenylpropyl, 3,4-dimethoxyphenyl, 4-ethyl-4'-biphenyl, 3,4,5-trimethoxyphenyl, propyl, hexyl, 2-propyl, (+/–)-2-butyl, isobutyl, 2-methylbutyl, isovaleryl, p-tolyl, p-anisyl, cyclohexyl, cyclohexylmethyl, cyclohexylpropyl, cycloheptyl, methyl, 2-methylcyclopropyl, cyclobutyl, cyclopentyl, cyclopentylethyl, 2-furyl, cyclohexylethyl, 4-methylcyclohexyl, 4-t-butylcyclohexyl, 4-methylcyclohexylmethyl, but-2-en-1-yl, 2-norbornylmethyl, or 2-thienyl.

Because combinatorial libraries can be screened while still bound to resin, additional embodiments of the invention include any of the above described combinatorial libraries bound to a solid-phase resin. The compounds in such libraries would be resin-bound through the imine nitrogen in the above Formulae and, therefore, the guanidine would be positively charged while bound to the resin. The resins to which such compounds can be bound are functionalized amine resins, solid-phase resins cross-linked with amino groups, in which case it would be appreciated by those in the art that the amine function can be cleaved from the resin during standard hydrogen fluoride (HF) cleavage procedures and retained with the subject compounds.

In the above Formulae the stereochemistry of the relevant chiral $R^1$ through $R^4$ groups can independently be in the R or S configuration, or a mixture of the two. For instance, as will be described in further detail below the $R^1$ and $R^2$ groups in Formula I and the $R^1$, $R^2$ and $R^3$ groups in Formula II are the side chains of the α-carbon of various amino acids. The amino acids can be in the L- or D-configuration, resulting in the same R group, varying only in its stereochemistry.

In the above Formulae, the term "$C_1$ to $C_{10}$ alkyl" denotes such radicals as methyl, ethyl, n-propyl, isopropyl, n-butyl, sec-butyl, tert-butyl, amyl, tert-amyl, hexyl, heptyl and the like. A preferred "$C_1$ to $C_{10}$ alkyl" group is methyl.

The term "$C_2$ to $C_{10}$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "$C_2$ to $C_{10}$ alkynyl" denotes such radicals as ethynyl, propynyl, butynyl, pentynyl, hexynyl, heptynyl, as well as di- and tri-ynes.

The term "substituted" as it is used in "$C_1$ to $C_{10}$ substituted alkyl," "$C_2$ to $C_{10}$ substituted alkenyl," and "$C_2$ to $C_{10}$ substituted alkynyl," denotes that the above $C_1$ to $C_{10}$ alkyl groups and $C_2$ to $C_{10}$ alkenyl and alkynyl groups are substituted by one or more, and preferably one or two, halogen, hydroxy, protected hydroxy, $C_3$ to $C_7$ cycloalkyl, $C_3$ to $C_7$ substituted cycloalkyl, naphthyl, substituted naphthyl, adamantyl, abietyl, thiofuranyl, indolyl, substituted indolyl, norbornyl, amino, protected amino, (monosubstituted)amino, protected (monosubstituted) amino, (disubstituted)amino, guanidino, (monosubstituted) guanidino, (disubstituted)guanidino, (trisubstituted) guanidino, imidazolyl, pyrolidinyl, $C_1$ to $C_7$ acyloxy, nitro, heterocycle, substituted heterocycle, $C_1$ to $C_4$ alkyl ester, carboxy, protected carboxy, carbamoyl, carbamoyloxy, carboxamide, protected carboxamide, cyano, methylsulfonylamino, methylsulfinyl, methylsulfonyl, sulfurhydryl, $C_1$ to $C_4$ alkylthio, $C_1$ to $C_4$ alkyl sulfonyl or $C_1$ to $C_4$ alkoxy groups. The substituted alkyl groups may be substituted once or more, and preferably once or twice, with the same or with different substituents.

Examples of the above substituted alkyl groups include the cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allylcaroxybonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(isopropyl), 2-carbamoyloxyethyl, chloroethyl, bromoethyl, fluoroethyl, iodoethyl, chloropropyl, bromopropyl, fluoropropyl, iodopropyl and the like.

In preferred embodiments of the subject invention, preferred groups include $C_1$ to $C_{10}$ alkyl, $C_2$ to $C_{10}$ alkenyl, $C_2$ to $C_{10}$ alkynyl, $C_1$ to $C$substituted alkyl, $C_2$ to $C_{10}$ substituted alkenyl, or $C_2$ to $C_{10}$ substituted alkynyl and, regarding alkyl or substituted alkyl groups, more preferably $C_1$ to $C_7$, and even more preferably, $C_1$ to $C_6$. However, it would be appreciated to those of skill in the art that one or a few carbons could be added to an alkyl, alkenyl, alkynyl, substituted or unsubstituted, without substantially modifying the structure and function of the subject compounds and that, therefore, such additions would not depart from the spirit of the invention.

The term "$C_1$ to $C_4$ alkoxy" as used herein denotes groups such as methoxy, ethoxy, n-propoxy, isopropoxy, n-butoxy, t-butoxy and like groups. A preferred $C_1$ to $C_4$ alkoxy group is methoxy.

The term "$C_1$ to $C_1$ acyloxy" denotes herein groups such as formyloxy, acetoxy, propanoyloxy, butanoyloxy, pentanoyloxy, hexanoyloxy, heptanoyloxy, and the like.

Similarly, the term "$C_1$ to $C_7$ acyl" encompasses groups such as formyl, acetyl, propionoyl, butyroyl, pentanoyl, hexanoyl, heptanoyl, benzoyl and the like.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, phenyl, substituted phenyl, heterocycle, substituted heterocycle, $C_1$ to $C_{10}$ alkyl, $C_1$ to $C_4$ alkoxy, carboxy, protected carboxy, amino, or protected amino.

The substituent term "$C_3$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "$C_3$ to $C_7$ substituted cycloalkenyl" denotes the above $C_3$ to $C_7$ cycloalkenyl rings substituted by a $C_1$ to $C_{10}$ alkyl radical, halogen, hydroxy, protected hydroxy, $C_1$ to $C_4$ alkoxy, carboxy, protected carboxy, amino, or protected amino.

The term "heterocyclic ring" or "heterocycle" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred. Preferred heterocyclic rings include pyridinyl, pyrimidinyl, pyrazinyl, furanyl, imidazolyl and thiofuranyl rings. The heterocycles can be substituted or unsubstituted as, for example, with such substituents as those described in relation to substituted phenyl or substituted naphthyl.

The term "$C_7$ to $C_{16}$ phenylalkyl" denotes a $C_1$ to $C_{10}$ alkyl group substituted at any position by a phenyl ring. Examples of such a group include benzyl, 2-phenylethyl, 3-phenyl-(n-prop-1-yl), 4-phenyl-(-hex-1-yl), 3-phenyl-(n-am-2-yl), 3-phenyl-(sec-butyl), and the like. A preferred group is the benzyl group.

The term "$C_7$ to $C_{16}$ substituted phenylalkyl" denotes a $C_7$ to $C_{16}$ arylalkyl group substituted on the $C_1$ to $C_{10}$ alkyl portion with one or more, and preferably one or two, groups chosen from halogen, hydroxy, protected hydroxy, keto, $C_2$ to $C_3$ cyclic ketal, phenyl, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_{10}$ alkyl, $C_1$ to $C_6$ substituted alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, amino, (monosubstituted)amino, (disubstituted)amino, a N-(methylsulfonylamino) group, or a phenyl group, substituted or unsubstituted, for a resulting biphenyl group. When either the $C_1$ to $C_{10}$ alkyl portion or the phenyl portion or both are mono- or di-substituted the substituents can be the same or different.

Examples of the term "$C_7$ to $C_{16}$ substituted phenylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethylphenyl)-3-(aminomethyl)(n-pent-2-yl), 5-phenyl-3-keto-(n-pent-1-yl), 4-(4-aminophenyl)-4-(1,4-oxetanyl)(n-but-1-yl), and the like.

The term "$C_7$ to $C_{16}$ phenylalkenyl" denotes a $C_1$ to $C_{10}$ alkenyl group substituted at any position by a phenyl ring. The term "$C_7$ to $C_{16}$ substituted phenylalkenyl" denotes a $C_7$ to $C_{16}$ arylalkyl group substituted on the $C_1$ to $C_{10}$ alkenyl portion. Substituents can the same as those as defined above in relation to $C_7$ to $C_{16}$ phenylalkyl and $C_7$ to $C_{16}$ substituted phenylalkyl.

The term "substituted phenyl" specifies a phenyl group substituted with one or more, and preferably one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_4$ alkoxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, trifluoromethyl, N-(methylsulfonylamino), or phenyl, substituted or unsubstituted, such that, for example, a biphenyl results.

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected-hydroxy derivatives thereof and the like; a nitrophenyl group such as 3-or 4-nitrophenyl; a cyanophenyl group for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-prop-1-yl)phenyl and the like; a mono or di(alkoxyl)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methylphenoxy)phenyl, and the like,; 3-or 4-trifluoromethylphenyl; a mono- or dicarboxyphenyl or (protected carboxy)phenyl group such as 4-carboxyphenyl or 2,4-di(protected carboxy)phenyl; a mono-or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl) phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "substituted benzyl" means a benzyl group substituted with one or more, and preferably one or two, moieties chosen from the same groups as provided with reference to "substituted phenyl." Examples of substituted benzyl include 4-bromobenzyl, 4-chlorobenzyl, 4-fluorobenzyl, 4-ethoxybenzyl, 4-hydroxybenzyl, 4-iodobenzyl, and the like.

The term "substituted naphthyl" specifies a naphthyl group substituted with one or more, and preferably one or two, moieties chosen from the groups consisting of halogen, hydroxy, protected hydroxy, cyano, nitro, $C_1$ to $C_{10}$ alkyl, $C_1$ to $C_4$ alkoxy, carboxy, protected carboxy, carboxymethyl, protected carboxymethyl, hydroxymethyl, protected hydroxymethyl, amino, protected amino,(monosubstituted) amino, protected (monosubstituted)amino, (disubstituted) amino trifluoromethyl or N-(methylsulfonylamino). Examples of substituted naphthyl include 2-(methoxy)-naphthyl and 4-(methoxy)naphthyl.

The term "substituted indolyl" specifies a indolyl group substituted, either at the nitrogen or carbon, or both, with one or more, and preferably one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_{10}$ alkenyl, $C_7$ to $C_{16}$ phenylalkyl, $C_7$ to $C_{16}$ substituted phenylalkyl, $C_1$ to $C_6$ alkoxy, $C_1$ to $C_7$ acyl, alkyl carboxy, protected carboxy, carboxymethyl, protected carboxymethyl, hydroxymethyl, protected hydroxymethyl, formyl, amino, protected amino, monosubstituted amino, or disubstituted amino.

Examples of the term "substituted indolyl" include such groups as 6-fluoro, 5-fluoro, 5-bromo, 5-hydroxy, 5-methyl, 6-methyl, 7-methyl, 1-methyl, 1-ethyl, 1-benzyl, 1-napth-2-ylmethyl, and the like. An example of a disubstituted indolyl is 1-methyl-5-methyl indolyl.

The terms "halo" and "halogen" refer to the fluoro, chloro, bromo or iodo groups.

The term "(monosubstituted)amino" refers to an amino group with one substituent chosen from the groups consisting of phenyl, substituted phenyl, $C_1$ to $C_{10}$ alkyl, and $C_7$ to $C_{16}$ arylalkyl, wherein the latter three substituent terms are as defined above. The (monosubstituted)amino can additionally have an amino-protecting group as encompassed by the term "protected (monosubstituted)amino."

The term "(disubstituted)amino" refers to amino groups with two substituents chosen from the group consisting of phenyl, thiocarbonylimidazole, substituted phenyl, $C_1$ to $C_{10}$ alkyl, and $C_7$ to $C_{16}$ arylalkyl wherein the latter three substituent terms are as described above. The two substituents can be the same or different.

The terms "(monosubstituted)guanidino," "(disubstituted)guanidino," and "(trisubstituted)guanidino" are where the guanidino groups is substituted with one, two, or three substituents, respectively. The substituents can be any of those as defined above in relation to (monosubstituted)amino and (disubstituted)amino and, where more than one substituent is present, the substituents can be the same or different.

The term "amino-protecting group" as used herein refers to substituents of the amino group commonly employed to block or protect the amino functionality while reacting other functional groups on the amine component. The term "protected (monosubstituted)amino" means there is an amino-protecting group on the monosubstituted amino nitrogen atom. In addition, the term "protected carboxamide" means there is an amino-protecting group replacing the proton so that there is no N-alkylation. Examples of such amino-protecting groups include the formyl ("For") group, the trityl group (Trt), the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl)propyl(2)oxycarbonyl ("Bpoc"), 2-phenylpropyl(2)oxycarbonyl ("Poc"), 2-(4-xenyl)isopropoxycarbonyl, 1,1-diphenylethyl(1)-oxycarbonyl, 1,1-diphenylpropyl(1)oxycarbonyl, 2-(3,5-dimethoxyphenyl)propyl(2)oxycarbonyl ("Ddz"), 2-(p-toluyl)propyl(2)oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphine)ethoxycarbonyl, 9-fluoroenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl(2)propoxycarbonyl, cyclopropylmethoxycarbonyl, isobornyloxycarbonyl, 1-piperidyloxycarbonyl, benzyloxycarbonyl ("Z"), 4-phenylbenzyloxycarbonyl, 2-methylbenzyloxycarbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl, and the like; the benzoylmethylsulfonyl group, dithiasuccinoyl ("Dts"), the 2-(nitro)phenylsulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc and Fmoc. Further examples of amino-protecting groups embraced to by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-timethoxytrityl, 2-phenylprop-2-yl, trimethylsilyl, t-butyldimethylsilyl, 2,2,2-trichloroethyl, β-(trimethylsilyl)ethyl, β-(di(n-butyl)methylsilyl)ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the bicyclic guanidine. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The substituent term "$C_1$ to $C_4$ alkylthio" refers to sulfide groups such as methylthio, ethylthio, n-propylthio, iso-propylthio, n-butylthio, t-butylthio and like groups.

The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

Phenylthio, phenyl sulfoxide, and phenylsulfonyl compounds are known in the art and these terms have their art recognized definition. By "substituted phenylthio," "substituted phenyl sulfoxide," and "substituted phenylsulfonyl" is meant that the phenyl can be substituted as described above in relation to "substituted phenyl."

The substituent terms "cyclic $C_2$ to $C_{10}$ alkylene," "substituted cyclic $C_2$ to $C_{10}$ alkylene," "cyclic $C_2$ to $C_{10}$ heteroalkylene," and "substituted cyclic $C_2$ to $C_{10}$ heteroalkylene," defines such a cyclic group bonded ("fused") to the phenyl radical. The cyclic group may be saturated or contain one or two double bonds. Furthermore, the cyclic group may have one or two methylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, keto, ketal, $C_1$ to $C_4$ alkoxycarbonyl, formyl, $C_2$ to $C_4$ alkanoyl, $C_1$ to $C_{10}$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The substituent term "$C_1$ to $C_4$ alkylsulfoxide" indicates sulfoxide groups such as methylsulfoxide, ethylsulfoxide, n-propylsulfoxide, iso-propylsulfoxide, n-butylsulfoxide, sec-butylsulfoxide, and the like.

The cyclic alkylene or heteroalkylene group fused onto the benzene radical can contain two to ten ring members, but it preferably contains four to six members. Examples of such saturated cyclic groups are when the resultant bicyclic ring system is 2,3-dihydroindanyl and a tetralin ring. When the cyclic groups are unsaturated, examples occur when the resultant bicyclic ring system is a naphthyl ring or indanyl. An example of a cyclic group which can be fused to a phenyl radical which has two oxygen atoms and which is fully saturated is dioxanyl. Examples of fused cyclic groups which each contain one oxygen atom and one or two double bonds are when the phenyl ring is fused to a furo, pyrano, dihydrofurano, or dihydropyrano ring. Examples of cyclic groups which each have one nitrogen atom and contain one or two double more double bonds are when the phenyl is fused to a pyridino or pyrano ring. An example of a fused ring system having one nitrogen and two phenyl radicals is a carbozoyl group. Examples of cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring.

One or more of the bicyclic guanidines within a given combinatorial library may be present as a pharmaceutically acceptable salt. The term "pharmaceutically-acceptable salt" encompasses those salts that form with the carboxylate anions and include salts formed with the organic and inorganic cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)ammonium, phenylethylbenzylammonium, dibebenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. A preferred cation for the carboxylate anion is the sodium cation.

The compounds of the above Formulae can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more bicyclic guanidines can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, iso-propoxymethyl and the like; the α-($C_1$ to $C_4$) alkoxyethyl groups, for example methoxyethyl, ethoxyethyl, propxyethyl, iso-propoxyethyl, and the like; the 2-oxo-1,3-dioxolen-4-ylmethyl groups, such as 5-methyl-2-oxo-1,3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, pivaloyloxyethyl, α-acetoxymethyl, and the like; the ethoxycarbonyl-1-methyl group; the α-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

As used herein, a "combinatorial library" is an intentionally created collection of differing molecules which can be prepared by the synthetic means provided below or otherwise and screened for biological activity in a variety of formats (e.g., libraries of soluble molecules, libraries of compounds attached to resin beads, silica chips or other solid supports). A "combinatorial library," as defined above, involves successive rounds of chemical syntheses based on a common starting structure. The combinatorial libraries can be screened in any variety of assays, such as those detailed below as well as others useful for assessing the biological activity of bicyclic guanidines. The combinatorial libraries will generally have at least one active compound and are generally prepared such that the compounds are in equimolar quantities.

Compounds disclosed in previous work that are not in a mixture are not part of a "combinatorial library" of the invention (see, for example, Wellner et al., DE 30 18 023 A1 (1981)). In addition, compounds that are in an unintentional or undesired mixture are not part of a "combinatorial library" of the invention.

A combinatorial library of the invention can contain two or more of the above-described bicyclic guanidine compounds. The invention further provides a combinatorial library containing five or more of the above-described bicyclic guanidine compounds. In another embodiment of the invention, a combinatorial library can contain ten or more of the above-described bicyclic guanidine compounds. In yet another embodiment of the invention, a combinatorial library can contain fifty or more of the above-described bicyclic guanidine compounds. If desired, a combinatorial library of the invention can contain 100,000 or more, or even 1,000,000 or more, of the above-described bicyclic guanidine compounds.

As will be described in further detail, one combinatorial library was prepared with the structure of Formula I where the $R^1$, $R^2$ and $R^3$ positions varied as described above and, in further detail, below. Moreover, as will be described in further detail, another combinatorial library was prepared with the structure of Formula II where the $R^1$, $R^2$, $R^3$ and $R^4$ positions varied as described above and, in further detail, below. It should be appreciated, however, that such combinatorial libraries can comprise several smaller "sub-libraries" or sets of mixtures of compounds, depending on the format of preparation and the varying R groups. Sublibraries are described in further detail below.

The bicyclic guanidine combinatorial library and compounds of Formula I can be prepared according to the general Reaction Scheme I in FIG. 1. The combinatorial libraries were prepared using solid-phase techniques. The solid-phase resin, here p-methylbenzhydrylamine resin (MBHA), is indicated in FIG. 1 by the large circle and dash. After the addition of a first protected amino acid (having side chain $R^1$) to the resin, the resin-bound amino acid is deprotected. Following neutralization, a second protected amino acid (having side chain $R^2$) is added using traditional solid phase peptide chemistry. Following amino deprotection, the resulting dipeptide is then acylated with one of a wide range of available carboxylic acids to obtain the acylated dipeptide. Exemplary amino acids and carboxylic acids are discussed in detail below.

The next key step in the synthetic process, as shown in FIG. 1, is the reduction of the amide groups of the acylated dipeptide using diborane in THF at 65° C. to generate three secondary amines. This method has been used to generate diverse chemical libraries using the "libraries from libraries" concept as described, for instance, in Ostresh et al. *Proc. Nat. Acad. Sci.*, 91:11138 (1994) and Cuervo et al. *In Peptides*, 1994, Proceedings of the 23rd European Peptide Symposium (Maia, H. L. S, ed): 465–466 (1995), each of which are incorporated herein by reference.

Cyclization to obtain the bicyclic guanidines can be performed using thiocarbonyldiimidazole ($CSIm_2$) as shown in FIG. 1 and as described in the ensuing Example. Alternatively, carbonyldiimidazole can be used under the same reaction conditions as those described for thiocarbonyldiimidazole in Example 1. Other reagents which can be used to achieve cyclization to form the bicyclic guanidine include phosgene, triphosgene and thiophosgene. For example, bicyclic guanidines can be formed by treatment of the reduced acylated dipeptide with 24-fold excess triphosgene for approximately fifteen minutes (0.1 M in dichloromethane anhydrous with 5-fold excess of DIEA over dipeptide). The solution can then be removed, the resin washed with dry dichloromethane for approximately twelve hours to let the cyclization go to completion. Similar procedures can be employed with thiophosgene if an equimolar amount of non-nucleophilic base such as diisopropylethylamine is added. Finally, as shown in FIG. 1, the compounds can be cleaved from the resin using standard hydrogen fluoride procedures.

Any variety of amino acids can be used with the present invention as described above to generate a vast array of bicyclic guanidines with different $R^1$ and $R^2$ groups. As described in the ensuing Example, forty nine different first Boc-protected amino acids were coupled to the resin, which amino acids contain $R^1$. The forty nine amino acids included Ala, Phe, Ile, Lys(Clz), Leu, Met(O), Arg(Tos), Val, Tyr (Brz), ala, phe, ile, lys(ClZ), leu, arg(Tos), val, tyr(Brz), α-Abu, α-Aib, Nva, nva, Nle, nle, Orn(Cbz), Nap, nap, Cha, cha, Met($O_2$), $pNO_2$-Phe, $pNO_2$-phe, pCl-Phe, pCl-phe, pF-Phe, pf-phe, Lys(Ac), Pya, pya, Chg, chg, tBu-Gly, $pNH_2$-Phe(Fmoc), $pNH_2$-phe(Fmoc), Tyr(Et), tyr(Et), pI-Phe, pI-phe, Tyr(Me), and tyr(Me). Fifty one different second Boc-protected amino acids were coupled, thereby providing fifty one various $R^2$ groups. Those fifty one amino acids included Ala, Phe, Gly, Ile, Lys(Clz), Leu, Met(O), Arg(Tos), Val, Tyr(Brz), ala, phe, ile, lys(Clz), leu, arg(Tos), val, tyr(Brz), α-Abu, Nve, nve, Nle, nle, Orn(Cbz), Nap, nap, Cha, cha, Met($O_2$), $pNO_2$-Phe, $pNO_2$-phe, pCl-Phe, pCl-phe, pF-Phe, pF-phe, Lys(Ac), Pya, pya, Chg, chg, tBu-Gly, $pNH_2$-Phe(Fmoc), $pNH_2$-phe(Fmoc), Tyr(Et), tyr (Et), Asp(Fm), asp(Fm), pI-Phe, pI-phe, Tyr(Me), and tyr (Me).

As used herein, abbreviations for the various amino acid side-chain protecting groups are as follows: "tBu" for tert-butyl, "Boc" for tert-butoxycarbonyl, "Brz" for 2-bromobenzyloxycarbonyl, "Clz" for 2-chlorobenzyloxycarbonyl, "Tos" for tosyl, "Cbz" for benzyloxycarbonyl, "Ac" for acetyl, "Fmoc" for fluorenylmethyloxycarbonyl, and "Fm" for fluorenylmethyl. These abbreviations and any others used herein are those which are commonly known and used in the field. Moreover, also as is commonly practiced in the field and with reference to the amino acid nomenclature, all lower case lettering herein means the D-form of the amino acid as opposed to the L-form. Other nomenclature and three-letter abbreviations used herein for amino acids and derivatives thereof, as well as their respective side chains are as follows:

TABLE 1

| AMINO ACID NAME | | |
|---|---|---|
| FULL | 3-LETTER CODE | SIDE CHAIN R (FOR $R^1$ AND $R^2$) |
| Alanine | Ala | —$CH_3$ |
| Phenylalanine | Phe | —$CH_2$—C6H5 (phenyl) |
| Glycine | Gly | —H |
| Isoleucine | Ile | —$CH(CH_3)CH_2CH_3$ |
| Lysine | Lys | —$(CH_2)_4NH_2$ |
| Leucine | Leu | —$CH_2CH(CH_3)_2$ |
| Methionine-sulfoxide | Met(O) | —$CH_2CH_2$—S(=O)—$CH_3$ |
| Methionine-sulfone | Met($O_2$) | —$CH_2CH_2$—S(=O)$_2$—$CH_3$ |
| Arginine | Arg | —$CH_2CH_2CH_2NHC(NH)NH_2$ |
| Valine | Val | —$CH(CH_3)_2$ |
| Tyrosine | Tyr | —$CH_2$—(C6H4)—OH |
| O-Methyl-Tyrosine | O-Me-Tyr or Tyr(Me) | —$CH_2$—(C6H4)—OMe |
| O-Ethyl-Tyrosine | O-Et-Tyr or Tyr(Et) | —$CH_2$—(C6H4)—OEt |
| α-Aminobutyric acid | α-Abu | —$CH_2$—$CH_3$ |
| α-Aminoisobutyric | α-Aib | —$(CH_3)_2$ |
| Norvaline | Nva | —$CH_2CH_2CH_3$ |
| Norleucine | Nle | —$CH_2CH_2CH_2CH_3$ |
| Ornithine | Orn | —$(CH_2)_3NH_2$ |
| Napthylalanine | Nap | —$CH_2$—naphthyl |
| Cyclohexylalanine | Cha | —$CH_2$—cyclohexyl |
| p-nitro-Phenylalanine | $pNO_2$-Phe | —$CH_2$—(C6H4)—$NO_2$ |
| p-chloro-Phenylalanine | pCl-Phe | —$CH_2$—(C6H4)—Cl |

TABLE 1-continued

| AMINO ACID NAME | | |
|---|---|---|
| FULL | 3-LETTER CODE | SIDE CHAIN R (FOR $R^1$ AND $R^2$) |
| p-fluoro-Phenylalanine | pF-Phe | —$CH_2$—(C6H4)—F |
| 3-Pyridylalanine | Pya | —$CH_2$—(3-pyridyl) |
| Cyclohexylglycine | Chg | cyclohexyl |
| t-butyl-Glycine | t-Bu-Gly | —$C(CH_3)3$ |
| p-amino-Phenylalanine | $pNH_2$-Phe | —$CH_2$—(C6H4)—$NH_2$ |
| p-iodo-Phenylalanine | pI-Phe | —$CH_2$—(C6H4)—I |
| Aspartic acid | Asp | —$CH_2COOH$ |

It should be appreciated from the above-described embodiments of $R^1$ and $R^2$, as well as from the described reaction scheme, that some of the amino acid side chains are modified during the synthesis. For instance some of the $R^1$ amino acid side chains are modified by the reduction steps. Similarly, certain $R^2$ groups are modified by the reduction procedures. Accordingly, with reference to the forty nine preferred embodiments of $R^1$ and the fifty one of $R^2$, they are described above and below, except in Table 1, in their modified form. For example, following reduction of a lysine side chain with a 2-chlorobenzyloxycarbonyl protecting group, an N-methylaminobutyl side chain would result. Following the guanidine formation step with thiocarbonyldiimidazole, this side chain would be further modified to form the N-methyl,N-thiocarbonylimidazole-aminobutyl functionality.

As well, a variety of carboxylic acids can be used in the acylation step of Reaction Scheme I, thereby generating a wide array of substituents at the $R^3$ position of the bicyclic guanidines. Exemplary carboxylic acids include the forty-one which were used in preparing the subject combinatorial libraries and compounds provided in the ensuing Example. Those forty one carboxylic acids include 3-phenylbutyric acid, m-toluylacetic acid, 3-fluorophenylacetic acid, p-toluylacetic acid, 4-fluorophenylacetic acid, 3-methoxyphenylacetic acid, 4-methoxyphenylacetic acid, 4-ethoxyphenylacetic acid, 3-(3,4-dimethoxyphenyl) propionic acid, 4-biphenylacetic acid, (3,4-dimethoxyphenyl)acetic acid, phenylacetic acid, hydrocinnamic acid, 4-phenylbutyric acid, butyric acid, heptanoic acid, isobutyric acid, (+/−)-2-methylbutyric acid, isovaleric acid, 3-methylvaleric acid, 4-methylvaleric acid, (tert-butyl) acetic acid, cyclohexylcarboxylic acid, cyclohexylacetic acid, cyclohexylbutyric acid, cycloheptylcarboxylic acid, lactic acid, acetic acid, cyclobutylcarboxylic acid, cyclopentylcarboxylic acid, 3-cyclopentylpropionic acid, cyclohexylpropionic acid, 4-methyl-1-cyclohexylcarboxylic acid, 4-(tert-butyl)-cyclohexylcarboxylic acid, 2-norbornylacetic acid, 1-adamantaneacetic acid, 2-ethylbutyric acid, (3,3-diphenyl)propionic acid, 2-methyl-4-nitro-1-imidazolepropionic acid, cyclopentylacetic acid, and indolyl-3-acetic acid.

Figure 2:
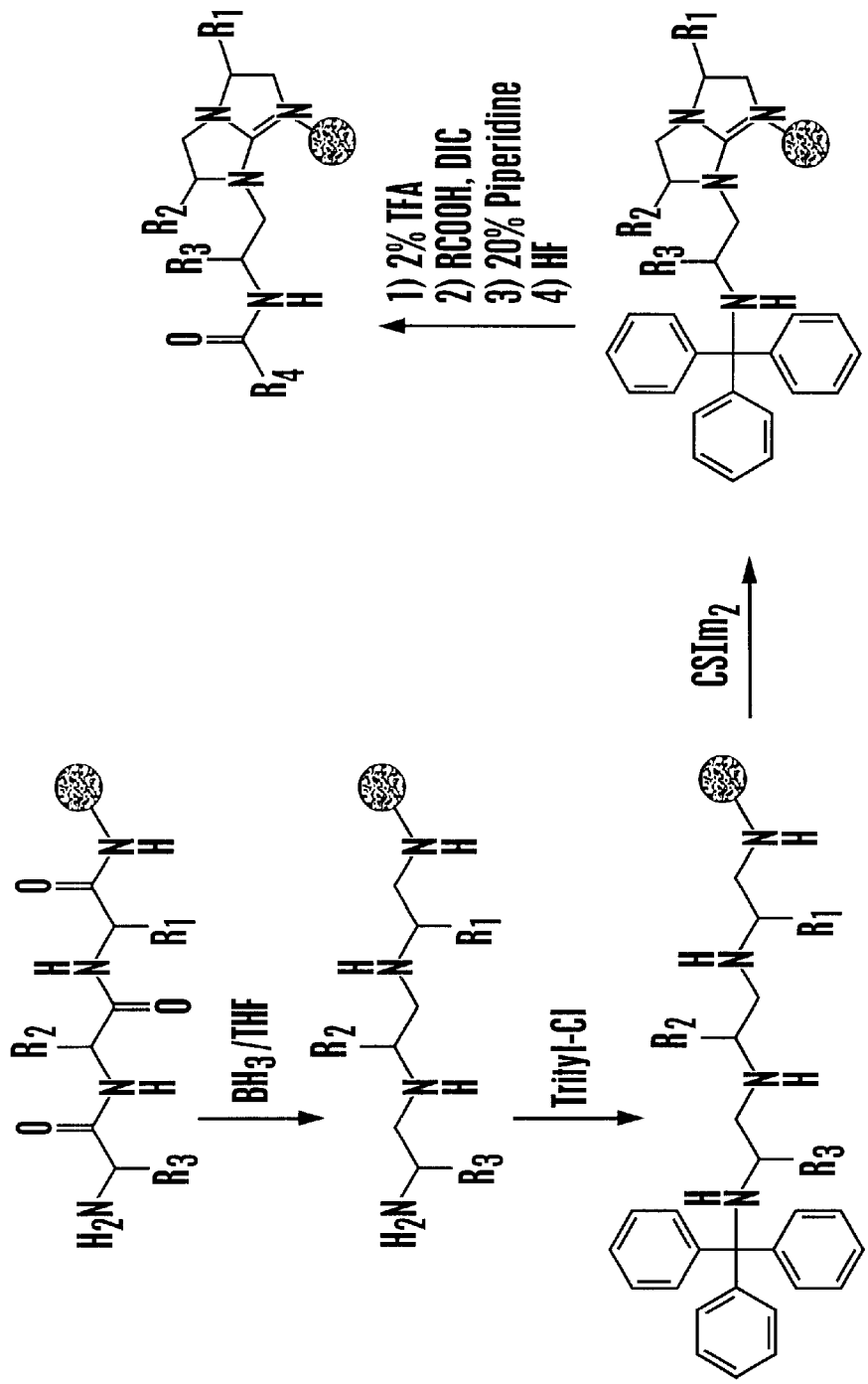
FIG. 2 shows the Reaction Scheme II for preparing combinatorial libraries and compounds of the present invention.

The bicyclic guanidine combinatorial library and compounds of Formula II can be prepared according to the general Reaction Scheme II in FIG. 2. The combinatorial libraries were prepared using solid-phase techniques. The solid-phase resin, here p-methylbenzhydrylamine resin (MBHA), is indicated in FIG. 2 by the circle and dash. Using traditional solid phase peptide chemistry, a first protected amino acid (having side chain $R^1$) is added to the resin. Following amino deprotection, a second protected amino acid (having side chain $R^2$) is added and then deprotected. A third protected amino acid (having side chain $R^3$) is then added and deprotected. Exemplary amino acids are discussed in detail below.

The next step in the synthetic process, as shown in FIG. 2, is the reduction of the amide groups of the tripeptide using borane in THF to generate three secondary amines. As discussed above, this method has been used to generate diverse chemical libraries using the "libraries from libraries" concept as described, for instance, in Ostresh et al. and Cuervo et al., supra. When reduction is complete, the N-terminus is selectively protected by a triphenylmethyl group. The three remaining secondary amines can be cyclized into a bicyclic guanidine using thiocarbonyldiimadazole ($CSIm_2$), as shown in FIG. 2. Other cyclizing reagents such as thiophosgene can be used, as discussed above regarding Reaction Scheme I.

The resulting positively charged resin-attached bicyclic guanidine can then be washed and the group protecting the N-terminus removed with a reagent such as 2% TFA. Following deprotection, the free N-terminus is acylated with one of a wide range of available carboxylic acid-derived acyl groups to obtain the acylated tripeptide. Exemplary carboxylic acids are discussed in detail below. The resin then can be treated to let the cyclization go to completion. Finally, as shown in FIG. 2, the compounds can be cleaved from the resin using standard hydrogen fluoride procedures.

Any variety of amino acids can be used with the present invention as described above to generate a vast array of bicyclic guanidines with different $R^1$, $R^2$ and $R^3$ groups. As described in ensuing Example II, thirty-four different first Boc-protected amino acids were coupled to the resin, which amino acids contain $R^1$. The thirty-four amino acids included Ala, ala, Phe, phe, Ile, ile, Leu, leu, Val, val, Tyr(Brz), tyr(Brz), α-Abu, Aib, Nva, nva, Nle, nle, Nal, nal, Cha, cha, pF-Phe, pf-phe, pCl-Phe, pCl-phe, Chg, chg, Tyr(OEt), tyr(OEt), pI-Phe, pI-phe, Tyr(OMe), and tyr(OMe). Thirty-four different second Boc-protected amino acids were coupled, thereby providing thirty-four various $R^2$ groups. Those thirty-four various amino acids included Ala, ala, Phe, phe, Ile, ile, Leu, leu, Val, val, Tyr(Brz), tyr(Brz), α-Abu, Nva, nva, Nle, nle, Nal, nal, Cha, cha, Met(O)$_2$, pF-Phe, pf-phe, pCl-Phe, pCl-phe, Chg, chg, Tyr(OEt), tyr(OEt), pI-Phe, pI-phe, Tyr(OMe), and tyr(OMe). Seventeen different third Boc-protected amino acids were coupled, thereby providing seventeen various $R^3$ groups. Those seventeen various amino acids included Ala, ala, Phe, phe, Gly, Leu, leu, Nva, nva, Nle, nle, Cha, cha, Tyr(OEt), tyr(OEt), Tyr(OMe), and tyr(OMe). As described above, all lower case lettering herein means the D-form of the amino acid as opposed to the L-form. Other nomenclature and three-letter abbreviations used herein for amino acids and derivatives thereof, as well as their respective side chains, are described in Table 1 above.

As well, a variety of carboxylic acids can be used in the acylation step of Reaction Scheme II, thereby generating a wide variety of substituents at the $R^4$ position of the bicyclic guanidines. Exemplary carboxylic acids that can be used as is or converted to the appropriate acylating agent include the seventy-one which were used in preparing the subject combinatorial libraries and compounds provided in Example II below. Those seventy-one carboxylic acids include 1-phenyl-1-cyclopropane carboxylic acid, 2-phenylbutyric acid, 3-phenylbutyric acid, m-toluylacetic acid, 3-fluorophenylacetic acid, 3-bromophenylacetic acid, (α,α,α-trifluoro-m-toluyl)acetic acid, p-toluylacetic acid, 3-methoxyphenylacetic acid, 4-bromophenylacetic acid, 4-methoxyphenylacetic acid, 4-ethoxyphenylacetic acid, 4-isobutyl-α-methylphenylacetic acid, 3,4-dichlorophenylacetic acid, 3-(3,4-dimethoxyphenyl)propionic acid, 4-biphenylacetic acid, α-methylcinnamic acid, 2-(trifluoromethyl)cinnamic acid, (3,4-dimethoxyphenyl)acetic acid, 3,4-(methylenedioxy)phenylacetic acid, 2-methoxycinnamic acid, benzoic acid, 4-chlorocinnamic acid, m-anisic acid, 4-isopropylbenzoic acid, 4-vinylbenzoic acid, 4-fluorobenzoic acid, 4-bromobenzoic acid, 3,4-dimethoxycinnamic acid, t-cinnamic acid, 3,4-dimethylbenzoic acid, 3-fluoro-4-methylbenzoic acid, 3-bromo-4-methylbenzoic acid, 3-iodo-4-methylbenzoic acid, 3,4-dichlorobenzoic acid, 4-biphenylcarboxylic acid, 3,4-difluorobenzoic acid, m-toluic acid, phenylacetic acid, hydrocinnamic acid, 3-methoxy-4-methylbenzoic acid, 4-phenylbutyric acid, 3,4-dimethoxybenzoic acid, 4-ethyl-4-biphenylcarboxylic acid, 3,4,5-trimethoxybenzoic acid, butyric acid, heptanoic acid, isobutyric acid, (+/−)-2-methylbutyric acid, isovaleric acid, 3-methylvaleric acid, 4-methylvaleric acid, p-toluic acid, p-anisic acid, cyclohexylcarboxylic acid, cyclohexylacetic acid, cyclohexylbutyric acid, cycloheptylcarboxylic acid, acetic acid, 2-methylcyclopropylcarboxylic acid, cyclobutylcarboxylic acid, cyclopentylcarboxylic acid, 3-cyclopentylpropionic acid, 2-furoic acid, cyclohexylpropionic acid, 4-methyl-1-cyclohexylcarboxylic acid, 4-t-butylcyclohexylcarboxylic acid, 4-methylcyclohexylacetic acid, tiglic acid, 2-norbornylacetic acid, and 2-thiophenecarboxylic acid.

The nonsupport-bound combinatorial library mixtures were screened in solution in radio-receptor inhibition assays and in an anti-bacterial assay, an anti-fungal assay, a calmodulin-dependent phosphodiesterase (CaMPDE) assay and a phosphodiesterase (PDE) assay described in detail below. Deconvolution of highly active mixtures can then be carried out by iterative or positional scanning methods. These techniques, the iterative approach or the positional scanning approach, can be utilized for finding other active compounds within the combinatorial libraries of the present invention using any one of the below-described assays or others well known in the art.

The iterative approach is well-known and is set forth in general in Houghten et al., *Nature*, 354, 84–86 (1991) and Dooley et al., *Science*, 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various combinatorial libraries as described, for example, in R. Houghten et al. PCT/US91/08694 and U.S. Pat. No. 5,556,762, both of which are incorporated herein by reference. The positional scanning approach is used as described below in the preparation and screening of the combinatorial libraries. In the positional scanning approach sublibraries are made defining only one variable with each set of sublibraries and all possible sublibraries with each single variable defined (and all other possibilities at all of the other variable positions), made and tested. From the instant description one skilled in the art could synthesize combinatorial libraries wherein two fixed positions are defined at a time. From the testing of each single-variable defined combinatorial library, the optimum substituent at that position is determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the new bicyclic guanidines, as well as methods of using the same, are included within the scope of the present invention. The new bicyclic guanidine compounds of the present invention can be used for a variety of purposes and indications and as medicaments for any such purposes and indications. For example, guanidine moieties are found in many biologically active compounds and, as described above, can be used to block hypotensive and adrenergic effects, E. J. Corey and Mitsuaki Ohtani, *Tetrahedron Letters.*, 30(39):5227–5230 (1989), incorporated herein by reference, or as sweeteners Nagarajan et al. *Synthetic Communications.*, 22(8):1191–1198 (1992), incorporated herein by reference. Additionally, as shown by the present invention, the subject compounds are useful as analgesics. Assays which can be, some of which have been, used to test the biological activity of the instant bicyclic guanidines include antimicrobial assays, a competitive enzyme-linked immunoabsorbent assay and radio-receptor assays, as described below and whose results are shown in Examples IV, V and VI.

The ability of the compounds to inhibit bacterial growth, and therefore be useful to that infection, can be determined by methods well known in the art. An exemplary in vitro antimicrobial activity assay is described in Blondelle and Houghten, *Biochemistry* 30:4671–4678 (1991), which is incorporated herein by reference. In brief, *Staphylococcus aureus* ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 $\mu$l of the culture solution using serial dilutions (e.g., $10^{-2}$, $10^{-3}$ and $10^{-4}$) onto solid agar plates. In 96-well tissue culture plates bicyclic guanidines, individual or in mixtures, are added to the bacterial suspension at concentrations derived from serial two-fold dilutions ranging from 1500 to 2.9 $\mu$g/ml. The plates are incubated overnight at 37° C. and the growth determined at each concentration by $OD_{620}$ nm. The $IC_{50}$ (the concentration necessary to inhibit 50% of the growth of the bacteria) can then be calculated.

The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 $\mu$l. After blocking, 25 $\mu$l of a 1.0 mg/ml solution of each bicyclic guanidine mixture of a synthetic combinatorial library (or individual bicyclic guanidine) is added, followed by MAb 125-10F3 (Appel et al., supra) (25 $\mu$l per well). The MAb is added at a fixed dilution in which the bicyclic guanidine in solution effectively competes for MAb binding with the antigenic peptide adsorbed to the plate. The remaining steps are the same as for direct ELISA. The concentration of bicyclic guanidine necessary to inhibit 50% of the MAb binding to the control peptide on the plate ($IC_{50}$) is determined by serial dilutions of the bicyclic guanidine.

Figure 3A:
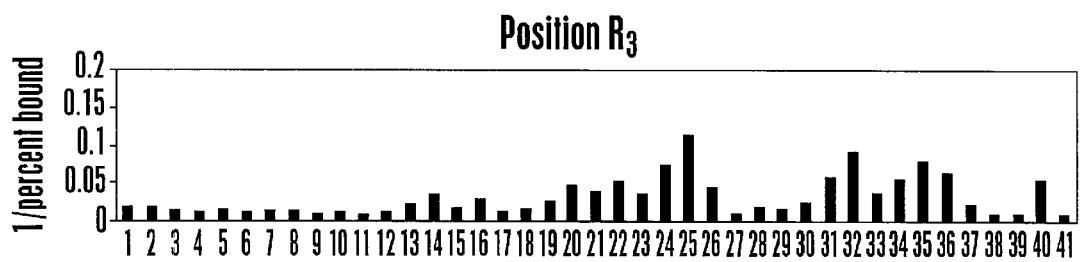
FIGS. 3A, 3B and 3C graphically depict the σ receptor assay binding data for a bicyclic guanidine combinatorial library of the subject invention.
Figure 3B:
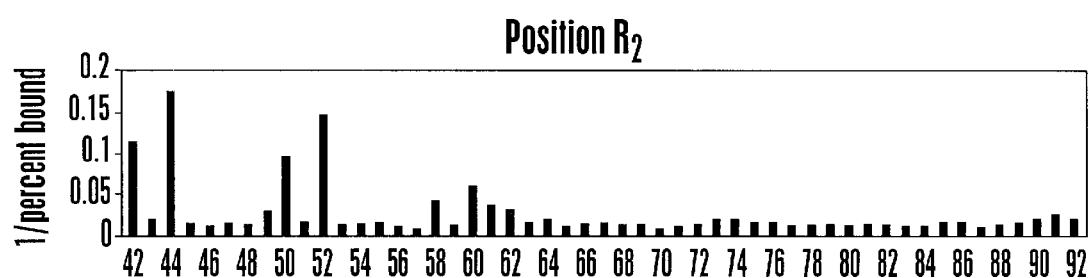
Figure 3C:
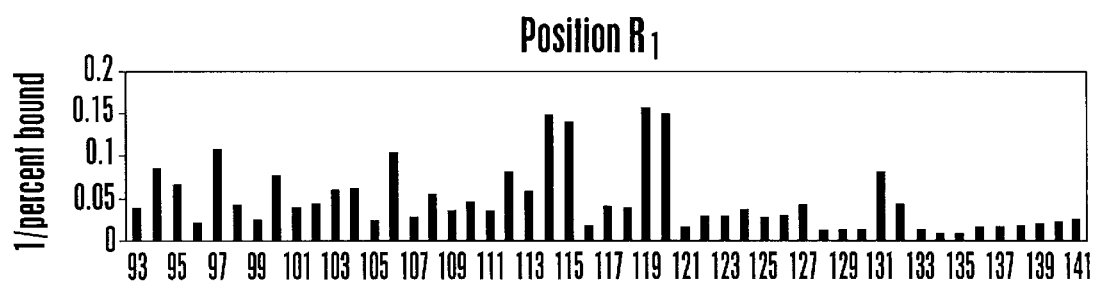
Figure 4A:
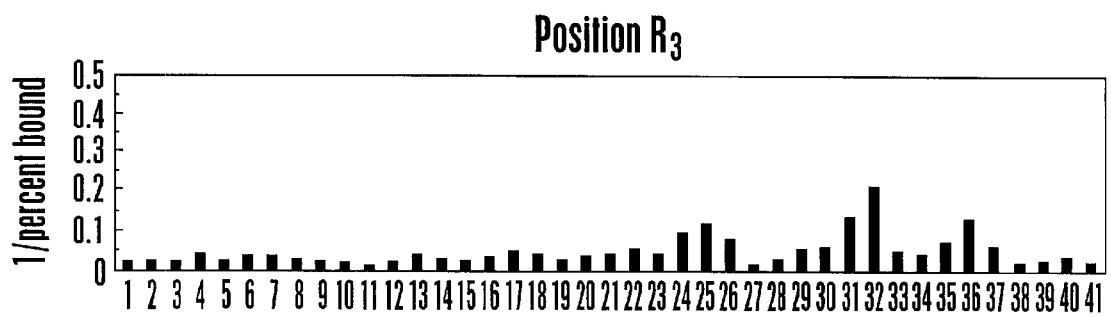
FIGS. 4A, 4B and 4C provide graphs depicting the κ-opioid receptor screening data for a bicyclic guanidine combinatorial library of the subject invention.
Figure 4B:
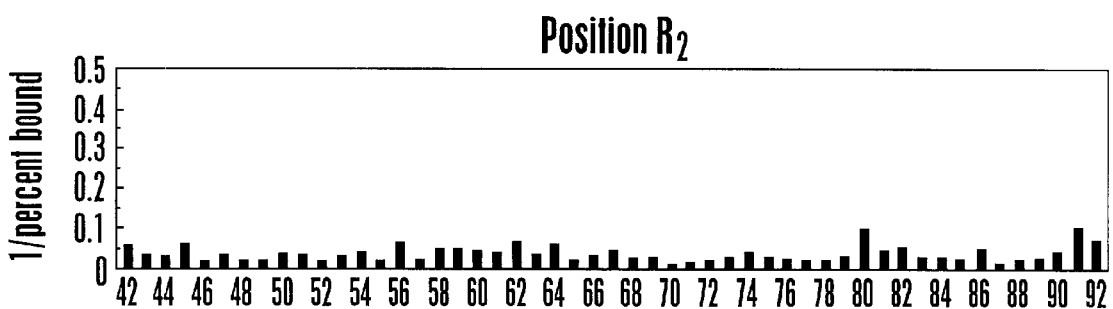
Figure 4C:
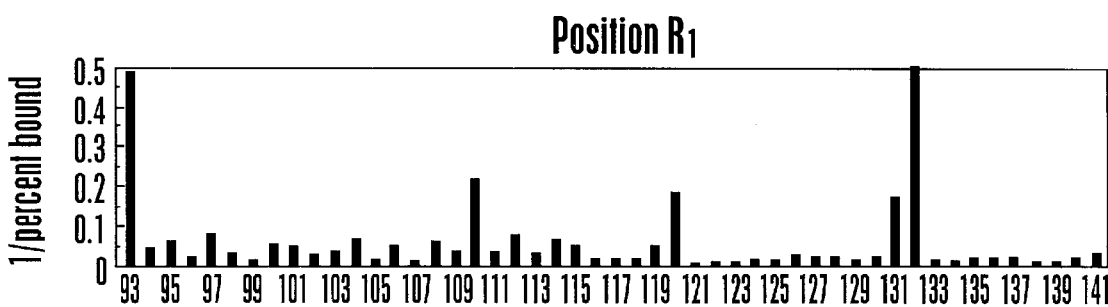

Alternative screening can be, and has been, done with radio-receptor assays as provided in Examples IV, V and VI and FIGS. 3 and 4. The radio-receptor assay, can be selective for any one of the $\mu$, $\kappa$, or $\delta$ opiate receptors. Therefore, the compounds of the present invention are useful in vitro for the diagnosis of relevant opioid receptor subtypes, such as $\kappa$, in the brain and other tissue samples. Similarly, the compounds can be used in vivo diagnostically to localize opioid receptor subtypes.

The radio-receptor assays are also an indication of the compounds' analgesic properties as described, for example, in Dooley et al., *Proc. Natl. Acad. Sci.*, 90:10811–10815 (1993). For example, it can be envisioned that these compounds can be used for therapeutic purposes to block the peripheral effects of a centrally acting pain killer. For instance, morphine is a centrally acting pain killer. Morphine, however, has a number of deleterious effects in the periphery which are not required for the desired analgesic effects, such as constipation and pruritus (itching). While it is known that the many compounds do not readily cross the blood-brain barrier and, therefore, elicit no central effect, the subject compounds can have value in blocking the periphery effects of morphine, such as constipation and pruritus. Accordingly, the subject compounds are also useful as drugs, namely as analgesics, or to treat pathologies associated with other compounds which interact with the opioid receptor system.

Additionally, such compounds can be tested in a $\sigma$ receptor assay. Ligands for the $\sigma$ receptor can be useful as antipsychotic agents, as described in Abou-Gharbia et al., *Annual Reports in Medicinal Chemistry,* 28:1–10 (1993).

Radio-receptor assays, such as those whose results are shown in Examples IV, V and VI, below, can be performed with particulate membranes prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed.

Each brain is individually homogenized in 40 ml Tris-HCl buffer (50 mM, pH 7.4, 4° C.) and centrifuged (Sorvall® RC5C SA-600: Du Pont, Wilmington, Del.) (16,000 rpm) for 10 minutes. The pellets are resuspended in fresh Tris-HCl buffer and incubated at 37° C. for 40 minutes. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H-[D-Ala$^2$,Me-Phe$^4$,Gly-ol$^5$]enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 µg/ml of bicyclic guanidine, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the bicyclic guanidines, individually or in mixtures. IC$_{50}$ values (the concentration necessary to inhibit 50% of $^3$H-DAMGO binding) are then calculated. IC$_{50}$ values of less than 1000 nM are indicative of highly active opioid compounds which bind to the µ receptor, with particularly active compounds having IC$_{50}$ values of 100 nM or less and the most active compounds with values of less than 10 nM.

As opposed to this µ receptor selective assay, which can be carried out using $^3$H-DAMGO as radioligand, as described above, assays selective for κ receptors can be carried out using [$^3$H]-U69,593 (3 nM, specific activity 62 Ci/mmol) as radioligand. Assays selective for δ opiate receptors can be carried out using tritiated DSLET ([D-Ser$^2$, D-Leu$^5$]-threonine-enkephalin) as radioligand. Assays selective for the σ opiate receptor can use radiolabeled pentazocine as ligand.

Figure 5A:
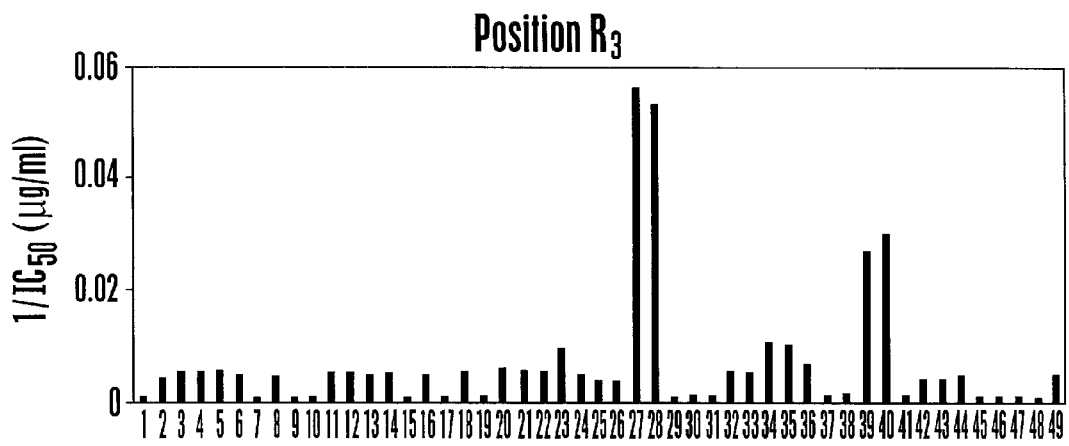
FIGS. 5A, 5B and 5C provide graphs depicting the antifungal activity screening data for a bicyclic guanidine combinatorial library of the subject invention.
Figure 5B:
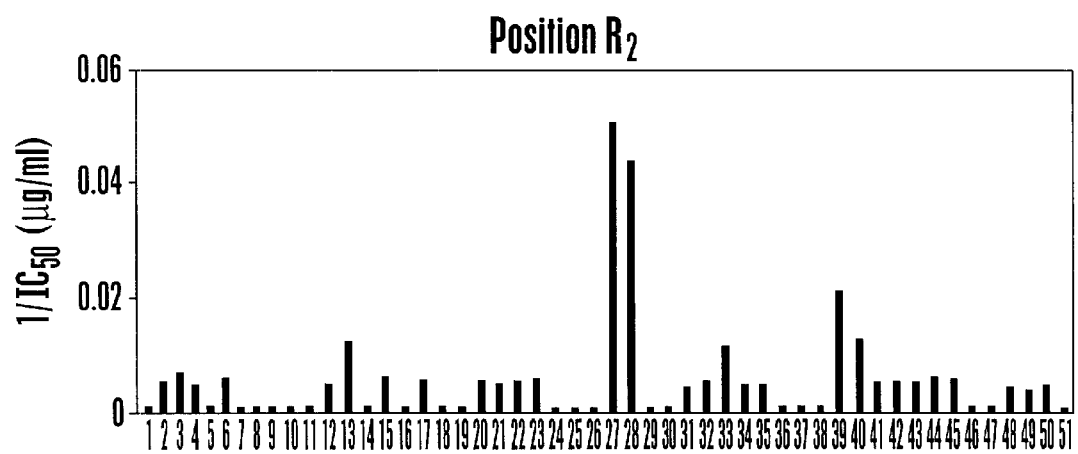
Figure 5C:
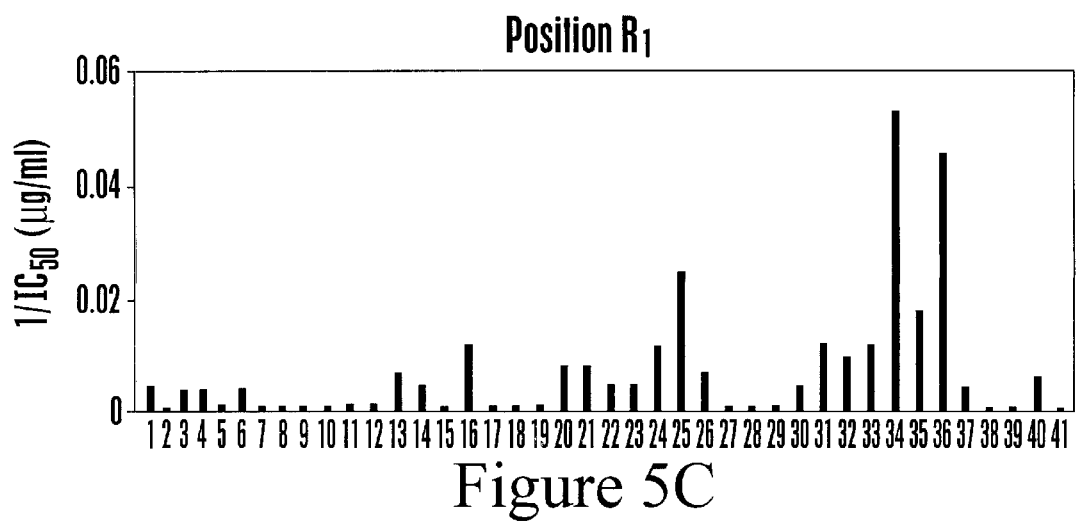

Screening of combinatorial libraries and compounds of the invention also can be, and has been, done with an anti-fungal assay as provided in Examples VII and VIII and FIG. 5. Many compounds were shown to be active. Therefore, compounds of the present invention are useful for treating fungal infections.

Fungal infections, including life threatening infections cause by pathogenic fungi, are becoming increasingly common, especially in those individuals with suppressed immune systems such as those with cancer or AIDS. In particular, *Candida albicans* and *Cryptococcus neoformans* are two of the most common fungi responsible for infections. Candidiasis is the fungal infection most frequently associated with HIV-positive patients. Cryptococcosis is the leading cause of morbidity and mortality due to fungi in those with AIDS. The compounds of the subject invention are useful for treating these, as well as other, fungal infections.

An example of an anti-fungal assay is the one whose results are shown in Examples VII and VIII, below. Microdilution assays can be carried out against *Candida albicans* (ATCC 10231) in ninety-six-well tissue culture plates, as described in Blondelle et al., *J. Appl. Bacteriol.*, 78:39 (1995). In brief, the yeast culture are spread on YM agar plates and incubated at 30° C. for 48 hours prior to the assay. Two colonies of this culture (each 1 mm in diameter) are then seeded in 5 ml of 2×YM broth, vortex-mixed and diluted 10-fold in 2×YM broth, for an approximate final concentration of 10$^5$ to 5×10$^5$ CFU/ml. The actual *Candida albicans* concentration are determined by plating on agar plates as described above. Yeast suspension in 2×broth are added to the mixtures at varying concentrations derived from serial two-fold dilutions. The plates are then incubated for 48 hours at 30° C. The relative percent growth of the yeast found for each mixture can be determined by the optical density at 620 nm (OD$_{620}$) using a Titertek Multiskan Plus apparatus. The IC$_{50}$ values then can be calculated using a sigmoidal curve fitting software (Graphpad, ISI Software, San Diego, Calif.). The minimum inhibitory concentration (MIC), which is defined as the lowest concentration of mixture at which no change in OD$_{620}$ occurs between 0 and 48 hours, also can be determined.

A bicyclic guanidine synthetic combinatorial library was assayed in positional scanning format for antifungal activity against *Candida albicans*. Each mixture was screened at four concentrations varying from 250 to 31.25 µg/ml or, for the most active mixtures, at eight concentrations varying from 250 to 1.95 µg/ml and their IC$_{50}$ values determined (FIG. 5; and Table 12, Example VII). Following the screening, thirty-two individual compounds were synthesized and screened in a similar manner. The most active compounds showed MIC values of 3–8 µg/ml (Table 13, Example VIII).

Figure 6A:
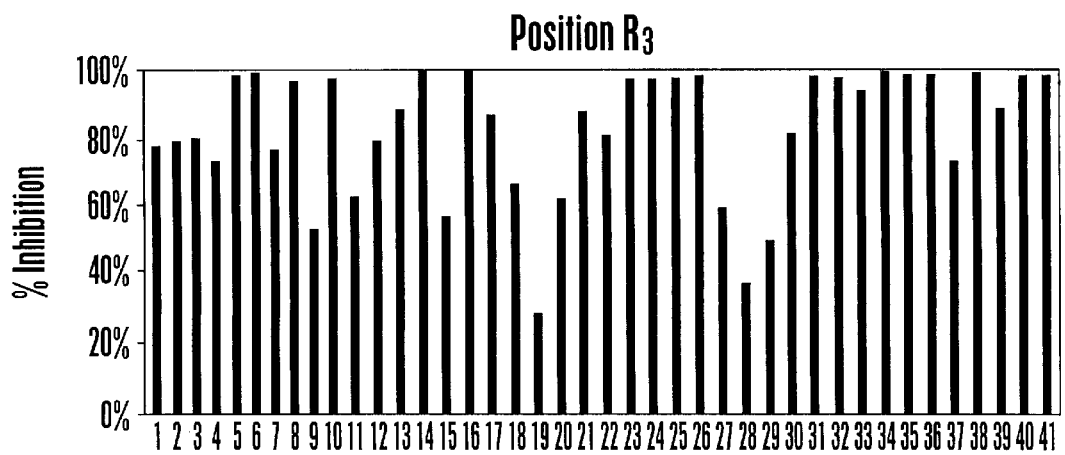
FIGS. 6A, 6B and 6C provide graphs depicting the inhibition of calmodulin activity screening data for a bicyclic guanidine combinatorial library of the subject invention.
Figure 6B:
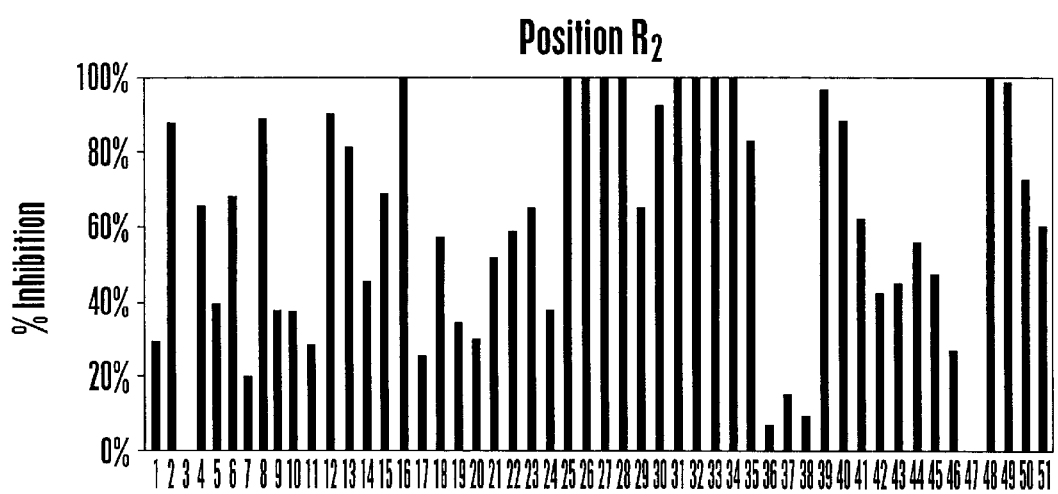
Figure 6C:
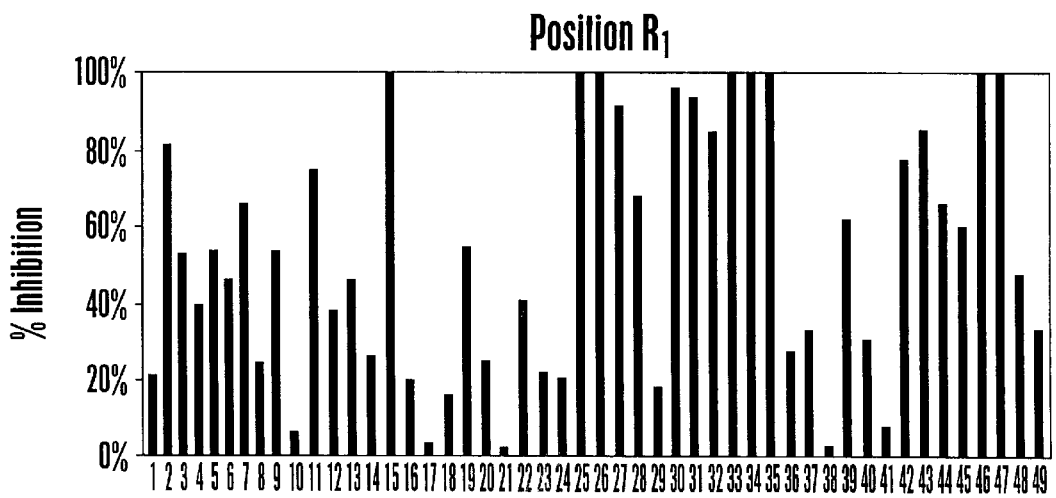

Screening of combinatorial libraries and compounds of the invention also can be, and has been, done with a calmodulin-dependent phosphodiesterase (CaMPDE) assay as provided in Examples IX to XII and FIG. 6. Many compounds were shown to be active. Therefore, compounds of the present invention are useful as calmodulin antagonists.

Calmodulin (CaM), which is the major intracellular calcium receptor, is involved in many processes that are crucial to cellular viability. In particular, calmodulin is implicated in calcium-stimulated cell proliferation. Calmodulin antagonists are, therefore, useful for treating conditions associated with increased cell proliferation, for example, cancer. In addition, calmodulin antagonists such as compounds of the subject invention are useful both in vitro and in vivo for identifying the role of calmodulin in other biological processes. The disadvantages of known antagonists such as trifluoperazine and N-(4-aminobutyl)-5-chloro-2-naphthalenesulfonamide (W13) include their non-specificity and toxicity. In contrast, advantages of the cyclic combinatorial libraries and compounds of the subject invention as calmodulin antagonists include their reduced flexibility and ability to generate broader conformational space of interactive residues as compared to their linear counterparts.

An example of an assay that identifies CaM antagonists is a CaMPDE assay, such as the one whose results are shown in Examples IX to XII, below. Samples are mixed with 50 µl of assay buffer (360 mM Tris, 360 mM Imidazole, 45 mM Mg(CH$_3$COO)$_2$, pH 7.5) and 10 µl of CaCl$_2$ (4.5 mM) to a final volume of 251 µl. 25 µl of calmodulin stock solution (Boehringer Mannheim; 0.01 µg/µl) is then added and the samples then sit at room temperature for 10 minutes. 14 µl of PDE (Sigma; 2 Units dissolved in 4 ml of water; stock concentration: 0.0005 Units/µl) is then added, followed by 50 µl of 5'-nucleotidase (Sigma; 100 Units dissolved in 10 ml of 10 mM Tris-HCl containing 0.5 mM Mg(CH$_3$COO)$_2$, pH 7.0; stock concentration: 10 Units/ml). The samples are then incubated for 10 minutes at 30° C. 50 µl of adenosine 3',5'-cyclic monophosphate (cAMP) (20 mM in water at pH 7.0) is added, the samples incubated for 1 hour at 30° C. and then vortexed. 200 µl of trichloroacetic acid (TCA) (55% in water) is added to a 200 µl sample aliquot, which is then vortexed and centrifuged for 10 minutes. 80 µl of the resulting supernatants of each sample is transferred to a 96-well plate, with 2 wells each containing 80 µl of each sample. 80 µl of ammonium molybdate (1.1% in 1.1N H$_2$SO$_4$) is then added to all the wells, and the OD of each were determined at 730 nm, with the values later subtracted to the final OD reading. 16 µl of reducing agent (6 g sodium bisulfite, 0.6 g sodium sulfite and 125 mg of 1-amino-2-naphtol-4-sulfonic acid in 50 ml of water) is then added to one of each sample duplicate and 16 µl of water is added to the other duplicate. After sitting for 1 hour at room temperature, the OD of each well is determined at 730 nm. The percent inhibition of calmodulin activity is then calculated for each sample, using as 0% inhibition a control sample containing all reagents without any test samples and as 100% inhibition a control sample containing test samples and all reagents except calmodulin. In addition, the percent inhibition of phosphodiesterase activity was determined by following a similar protocol as the CaMPDE assay described above, except not adding calmodulin to the sample mixture and calculating the percent inhibition by using as 0% inhibition a control reagent without any test samples and as 100% inhibition a control sample containing test samples and all reagents except cAMP.

A bicyclic guanidine synthetic combinatorial library was assayed in positional scanning format for activity as calmodulin antagonists, as described above. Each mixture contained 2,000 to 2,500 individual compounds. At 15 µl/mg, over half of the mixtures showed greater than 60% inhibition (FIG. 6; Table 14 of Example IX). The IC$_{50}$ values were then determined for the most active mixtures, which were screened at four different concentrations varying from 50 to 2 µl/mg (Table 15 of Example X).

Since a large number of known calmodulin antagonists are not specific to calmodulin but also interact with target enzymes, these active mixtures were also assayed for specificity toward calmodulin versus phosphodiesterase (Table 16 of Example XI). Based on this screening data, individual bicyclic guanidine compounds were assayed for inhibitory activities in a similar manner as the mixtures, with dilutions varying from 10 to 1 µl/mg. The IC$_{50}$ values of these individual compounds ranged from about 0.8 to about 12 µl/ml, which represents a 10 to 20-fold increase compared to known antagonists such as trifluoperazine.

The novel compounds of the subject invention can be incorporated into pharmaceutical compositions. As pharmaceutical compositions for effecting analgesia, treating infections, pain, or other indications known to be treatable by guanidines, the bicyclic guanidine compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active bicyclic guanidine. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

The following Examples are intended to illustrate but not limit the present invention.

Introduction

When using either the iterative or positional scanning approach to the synthesis of the instant combinatorial libraries, it is necessary at some point to expose either the solid phase alone or the solid phase bound to one or two amino acids, to a mixture of reactive subunits. Such subunits can be the first or second amino acid, or the activated carboxylic acid residue. As each individual subunit in the mixture may react at varying rates with the solid phase or the molecule bound to the solid phase, it is advantageous to know the relative reaction rate of each reactive subunit. Once such relative rates are known, the concentration of each reactive subunit can be adjusted accordingly in order to have approximately equimolar amounts of each reactive subunit couple with either the bare solid support or the molecule bound to the support. (For a further discussion of this point, see J. M. Ostresh et al., *Biopolymers*, 34:1661–1689 (1994), herein incorporated by reference).

The theory underpinning the methodology for determining the relative reaction rates used by Ostresh et al. in the above-mentioned Biopolymers article is set forth below.

Assuming that a large excess of the amino acid to be reacted with the Peptide which in turn is bound to the solid support is used, then the rate of such a reaction for amino acid 1 and amino acid 2 is expressed in Equations (1) and (2) below, respectively:

$$(\text{Peptide-AA}_1) = k_{AA-1} \times (AA_1) \tag{1}$$

wherein:

"Peptide"=Ala-Phe-Leu-;

$AA_1$=baseline amino acid; and $k_{AA-1}$=reaction constant of $AA_1$ with Peptide.

$$(\text{Peptide-AA}_2) = k_{AA-2} \times (AA_2) \tag{2}$$

wherein:

"Peptide"=Ala-Phe-Leu-;

$AA_2$=amino acid whose reaction rate with Peptide is to be compared to $AA_1$; and $k_{AA-2}$=reaction rate of $AA_2$ with the Peptide.

If $k_{AA-1}$ and $k_{AA-2}$ are different, then for any given period of time, more of the AA with the slower rate must be added to the mixture of reactive subunits so that the Peptide attached to the solid support will have reacted at that step with approximately equal amounts of $AA_1$ and $AA_2$. Thus, only relative rates are of importance, and can be determined using the following equations:

$$\frac{k_{AA-1}}{k_{AA-2}} = \frac{(peptide - AA_1) \times (AA_2)}{(peptide - AA_2) \times (AA_1)} \tag{3}$$

In order to simplify the calculations, a ten fold molar excess of both $AA_1$ and $AA_2$ are used in experiments coupling the AA in question to the solid support "Peptide"; allowing Equation 3 to be simplified to Equation 4:

$$\frac{k_{AA-1}}{k_{AA-2}} = \frac{(peptide - AA_1)}{(peptide - AA_2)} \tag{4}$$

on the assumption that $(AA_1)=(AA_2)$.

In order to determine the proper ratio of concentrations of $AA_1$ and $AA_2$ to use in a reaction mixture; Equations (3) and (4) are solved for $[AA_1]$ and $[AA_2]$ to give Equation (5):

$$\frac{(AA_2)}{(AA_1)} = \frac{k_{AA-1}(peptide - AA_2)}{k_{AA-2}(peptide - AA_1)} \tag{5}$$

Since equimolar concentrations of Peptide-$AA_1$ and Peptide-$AA_2$ are desired equation (5) simplifies to Equation (6):

$$\frac{(AA_2)}{(AA_1)} = \frac{k_{AA-1}}{k_{AA-2}} \tag{6}$$

The ratio in Equation (6) was determined using the following modification of the Biopolymers article procedure. Thus, instead of cleaving and hydrolysing the peptide with 6N hydrochloric acid, equimolar amounts of Peptide-$AA_1$ and Peptide-$AA_2$, each bound separately to the same type of solid support used in the reactions of $AA_1$ and $AA_2$, were mixed with the reaction mixtures. The peptides were then cleaved and analyzed by HPLC (5–65% B in 30 minutes, Vydac 218TP54, A:0.05% TFA/$H_2O$, B:0.05% TFA/ACN, 214 nm). Carboxylic acid ratios were generated using the same technique.

The relative ratios for the reactive amino acid and carboxylic acid subunits determined by the above methodology are set forth, respectively, in Tables 2 and 3 below. These ratios apply regardless of to which structure (Formula I or Formula II) or at which position the subunit is being added.

TABLE 2

Predetermined Ratios

| No. | Amino Acid | Ratio |
|---|---|---|
| 1 | Boc-L-Alanine | 0.95 |
| 2 | Boc-L-Phenylalanine | 0.81 |
| 3 | Boc-L-Isoleucine | 1.16 |
| 4 | Boc-L-Lysine (2-ClZ) | 1.05 |
| 5 | Boc-L-Leucine | 1.08 |
| 6 | Boc-L-Methionine (O) | 0.89 |
| 7 | Boc-L-Arginine (Tos) | 1.42 |
| 8 | Boc-L-Valine | 1.14 |
| 9 | Boc-L-Tyrosine(2-Brz) | 1.26 |
| 10 | Boc-D-alanine | 0.95 |
| 11 | Boc-D-phenylalanine | 0.81 |
| 12 | Boc-D-isoleucine | 1.16 |
| 13 | Boc-D-lysine (Clz) | 1.05 |
| 14 | Boc-D-leucine | 1.08 |
| 15 | Boc-D-arginine (Tos) | 1.42 |
| 16 | Boc-D-valine | 1.14 |
| 17 | Boc-D-tyrosine (Brz) | 1.26 |
| 18 | Boc-L-α-Aminobutyric acid | 0.94 |
| 19 | Boc-α-Aminoisobutyric acid | 1.66 |
| 20 | Boc-L-Norvaline | 1.15 |
| 21 | Boc-D-norvaline | 1.15 |
| 22 | Boc-L-norleucine | 1.15 |
| 23 | Boc-D-norleucine | 1.15 |
| 24 | Boc-L-Ornithine (Cbz) | 1.06 |
| 25 | Boc-L-Naphthylalanine | 0.55 |
| 26 | Boc-D-naphthylalanine | 0.55 |
| 27 | Boc-L-cyclohexylalanine | 1.50 |
| 28 | Boc-D-cyclohexylalanine | 1.50 |

TABLE 2-continued

Predetermined Ratios

| No. | Amino Acid | Ratio |
|---|---|---|
| 29 | Boc-L-Methionine sulfone | 0.90 |
| 30 | Boc-L-p-nitro-Phenylalanine | 1.00 |
| 31 | Boc-D-p-nitro-phenylalanine | 1.00 |
| 32 | Boc-L-p-chloro-Phenylalanine | 1.00 |
| 33 | Boc-D-p-chloro-phenylalanine | 1.00 |
| 34 | Boc-L-p-fluoro-Phenylalanine | 1.00 |
| 35 | Boc-D-p-fluoro-phenylalanine | 1.00 |
| 36 | Boc-L-Lysine (Ac) | 0.90 |
| 37 | Boc-L-(3-Pyridyl)alanine | 1.00 |
| 38 | Boc-D-(3-pyridyl)alanine | 1.00 |
| 39 | Boc-L-Cyclohexylglycine | 2.00 |
| 40 | Boc-D-cyclohexylglycine | 2.00 |
| 41 | Boc-L-α-tButylglycine | 2.00 |
| 42 | Boc-p-Fmoc-amino-L-Phenylalanine | 1.25 |
| 43 | Boc-p-Fmoc-amino-D-phenylalanine | 1.25 |
| 44 | Boc-O-Ethyl-L-Tyrosine | 1.20 |
| 45 | Boc-O-Ethyl-D-tyrosine | 1.20 |
| 46 | Boc-p-Iodo-L-Phenylalanine | 1.00 |
| 47 | Boc-p-Iodo-D-phenylalanine | 1.00 |
| 48 | Boc-O-Methyl-L-Tyrosine | 1.20 |
| 49 | Boc-O-Methyl-D-tyrosine | 1.20 |
| 50 | Boc-Glycine | 1.00 |
| 51 | Boc-L-Aspartic acid (Fm) | 1.00 |
| 52 | Boc-D-aspartic acid (Fm) | 1.00 |

TABLE 3

Predetermined Ratios

| No. | Carboxylic Acid | Ratio |
|---|---|---|
| 1 | 3-phenylbutyric acid | 2.6 |
| 2 | m-toluylacetic acid | 1.8 |
| 3 | 3-fluorophenylacetic acid | 0.84 |
| 4 | p-toluylacetic acid | 1.36 |
| 5 | 4-fluorophenylacetic acid | 1.04 |
| 6 | 3-methoxyphenylacetic acid | 1.17 |
| 7 | 4-methoxyphenylacetic acid | 1.8 |
| 8 | 4-ethoxyphenylacetic acid | 1.4 |
| 9 | 3-(3,4-dimethoxyphenyl)-propionic acid | 2.2 |
| 10 | 4-biphenylacetic acid | 1.4 |
| 11 | 3,4-dimethoxyphenylacetic acid | 1.44 |
| 12 | phenylacetic acid | 1 |
| 13 | hydrocinnamic acid | 2.5 |
| 14 | 4-phenylbutyric acid | 3 |
| 15 | butyric acid | 3.4 |
| 16 | heptanoic acid | 3.51 |
| 17 | isobutyric acid | 3.11 |
| 18 | 2-methylbutyric acid | 6.25 |
| 19 | isovaleric acid | 6.36 |
| 20 | 3-methylvaleric acid | 5.06 |
| 21 | 4-methylvaleric acid | 3.32 |
| 22 | (tert-butyl)acetic acid | 6 |
| 23 | cyclohexylcarboxylic acid | 3.51 |
| 24 | cyclohexylacetic acid | 3.95 |
| 25 | cyclohexylbutyric acid | 3.33 |
| 26 | cycloheptanecarboxylic acid | 2.6 |
| 27 | lactic acid | 0.25 |
| 28 | acetic acid | 2.65 |
| 29 | cyclobutanecarboxylic acid | 2.77 |
| 30 | cyclopentanecarboxylic acid | 3.03 |
| 31 | 3-cyclopentylpropionic acid | 3.71 |
| 32 | cychexylpropionic acid | 2.8 |
| 33 | 4-methyl-1-cyclohexylcarboxylic acid | 5.92 |
| 34 | 4-(tert-butyl)-cyclohexylcarboxylic acid | 6.64 |
| 35 | 2-norbornylacetic acid | 5.45 |
| 36 | 1-adamantaneacetic acid | 11.16 |
| 37 | 2-ethylbutyric acid | 6 |
| 38 | 3,3-diphenylpropionic acid | 2.8 |

TABLE 3-continued

Predetermined Ratios

| No. | Carboxylic Acid | Ratio |
|---|---|---|
| 39 | 2-methyl-4-nitro-1-imidazolepropionic acid | 0.81 |
| 40 | cyclopentylacetic acid | 3.96 |
| 41 | indole-3-acetic acid | 3 |
| 42 | 1-phenyl-1-cyclopropane carboxylic acid | 1.00 |
| 43 | 2-phenylbutyric acid | 1.20 |
| 44 | 3-bromophenylacetic acid | 0.61 |
| 45 | (α,α,α-trifluoro-m-toluyl) acetic acid | 0.61 |
| 46 | 4-isobutyl-α-methylphenylacetic acid | 1.70 |
| 47 | 3,4-dichlorophenylacetic acid | 0.81 |
| 48 | α-methylcinnamic acid | 1.95 |
| 49 | 2-(trifluoromethyl)cinnamic acid | 1.03 |
| 50 | 3,4-(methylenedioxy)-phenylacetic acid | 1.27 |
| 51 | 2-methoxycinnamic acid | 5.60 |
| 52 | benzoic acid | 1.28 |
| 53 | 4-chlorocinnamic acid | 2.95 |
| 54 | m-anisic acid | 1.52 |
| 55 | 4-isopropylbenzoic acid | 3.00 |
| 56 | 4-vinylbenzoic acid | 1.50 |
| 57 | 4-flourobenzoic acid | 1.22 |
| 58 | 4-bromobenzoic acid | 0.59 |
| 59 | 3,4-dimethoxycinnamic acid | 7.27 |
| 60 | t-cinnamic acid | 4.20 |
| 61 | 3,4-dimethylbenzoic acid | 2.44 |
| 62 | 3-fluoro-4-methylbenzoic acid | 0.75 |
| 63 | 3-bromo-4-methylbenzoic acid | 0.86 |
| 64 | 3-iodo-4-methylbenzoic acid | 0.64 |
| 65 | 3,4-dichlorobenzoic acid | 0.39 |
| 66 | 4-biphenylcarboxylic | 5.10 |
| 67 | 3,4-difluorobenzoic acid | 0.45 |
| 68 | m-toluic acid | 1.60 |
| 69 | 3-methoxy-4-methylbenzoic acid | 2.10 |
| 70 | 3,4-dimethoxybenzoic acid | 3.08 |
| 71 | 4-ethyl-4-biphenylcarboxylic acid | 0.92 |
| 72 | 3,4,5-trimethoxybenzoic acid | 1.46 |
| 73 | p-toluic acid | 2.28 |
| 74 | p-anisic acid | 5.38 |
| 75 | 2-methylcyclopropylcarboxylic acid | 2.42 |
| 76 | 2-furoic acid | 4.44 |
| 77 | 4-methylcyclohexylacetic acid | 4.79 |
| 78 | tiglic acid | 4.59 |
| 79 | 2-thiophenecarboxylic acid | 1.16 |

EXAMPLE I

This example provides the synthesis of a combinatorial library of the present invention according to Reaction Scheme I, which is shown in FIG. 1. The $R^1$, $R^2$ and $R^3$ groups varied as described above and below. Again, forty-nine first amino acids were used, generating at least forty-nine $R^1$ groups, depending on the modifications to the side chains. The amino acids used to generate the $R^1$ groups are again listed below in Table 4. Fifty-one second amino acids were used to generate the various $R^2$ groups, which amino acids are also again summarized in Table 4 below. Finally, the forty-one carboxylic acids used to acylate the dipeptides and generate the various $R^3$ groups are also listed again in Table 4. Therefore, Table 4 provides a summary of all the amino acids ($R^1$ and $R^2$) and carboxylic acid components ($R^3$) used in the preparation of the combinatorial library.

TABLE 4

SUMMARY OF REAGENTS USED TO GENERATE R GROUPS IN PREPARED LIBRARIES

|    | $R^1$        | $R^2$        | $R^3$                              |
|----|--------------|--------------|------------------------------------|
| 1  | Ala          | Ala          | 3-phenylbutyric acid               |
| 2  | Phe          | Phe          | m-toluylacetic acid                |
| 3  | Ile          | Gly          | 3-fluorophenylacetic acid          |
| 4  | Lys(Clz)     | Ile          | p-toluylacetic acid                |
| 5  | Leu          | Lys(Clz)     | 4-fluorophenylacetic acid          |
| 6  | Met(O)       | Leu          | 3-methoxyphenylacetic acid         |
| 7  | Arg(Tos)     | Met(O)       | 4-methoxyphenylacetic acid         |
| 8  | Val          | Arg(Tos)     | 4-ethoxyphenylacetic acid          |
| 9  | Tyr(Brz)     | Val          | 3-(3,4-dimethoxyphenyl)-propionic acid |
| 10 | ala*         | Tyr(Brz)     | 4-biphenylacetic acid              |
| 11 | phe          | ala*         | (3,4-dimethoxyphenyl)acetic acid   |
| 12 | ile          | phe          | phenylacetic acid                  |
| 13 | lys(Clz)     | ile          | hydrocinnamic acid                 |
| 14 | leu          | lys(Clz)     | 4-phenylbutyric acid               |
| 15 | arg(Tos)     | leu          | butyric acid                       |
| 16 | val          | arg(Tos)     | heptanoic acid                     |
| 17 | tyr(Brz)     | val          | isobutyric acid                    |
| 18 | α-Abu        | tyr(Brz)     | (+/−)-2-methylbutyric acid         |
| 19 | α-Aib        | α-Abu        | isovaleric acid                    |
| 20 | Nve          | Nve          | 3-methylvaleric acid               |
| 21 | nve          | nve          | 4-methylvaleric acid               |
| 22 | Nle          | Nle          | (tert-butyl)acetic acid            |
| 23 | nle          | nle          | cyclohexylcarboxylic acid          |
| 24 | Orn(Cbz)     | Orn(Cbz)     | cyclohexylacetic acid              |
| 25 | Nap          | Nap          | cyclohexylbutyric acid             |
| 26 | nap          | nap          | cycloheptanecarboxylic acid        |
| 27 | Cha          | Cha          | lactic acid                        |
| 28 | cha          | cha          | acetic acid                        |
| 29 | Met(O₂)      | Met(O₂)      | cyclobutanecarboxylic acid         |
| 30 | pNO₂-Phe     | pNO₂-Phe     | cyclopentanecarboxylic acid        |
| 31 | pNO₂-phe     | pNO₂-phe     | 3-cyclopentylpropionic acid        |
| 32 | pCl-Phe      | pCl-Phe      | cyclohexylpropionic acid           |
| 33 | pCl-phe      | pCl-phe      | 4-methyl-1-cyclohexylcarboxylic acid |
| 34 | pF-Phe       | pF-Phe       | 4-(tert-butyl)cyclohexylcarboxylic acid |
| 35 | pF-phe       | pF-phe       | 2-norbornylacetic acid             |
| 36 | Lys(Ac)      | Lys(Ac)      | 1-adamantaneacetic acid            |
| 37 | Pya          | Pya          | 2-ethylbutyric                     |
| 38 | pya          | pya          | 3,3-diphenylpropionic acid         |
| 39 | Chg          | Chg          | 2-methyl-4-nitro-1-imidazolepropionic acid |
| 40 | chg          | chg          | cyclopentylacetic acid             |
| 41 | tBu-Gly      | tBu-Gly      | indole-3-acetic acid               |
| 42 | pNH₂-Phe (Fmoc) | pNH₂-Phe (Fmoc) |                              |
| 43 | pNH₂-phe (Fmoc) | pNH₂-phe (Fmoc) |                              |
| 44 | Tyr(Et)      | Tyr(Et)      |                                    |
| 45 | tyr(Et)      | tyr(Et)      |                                    |
| 46 | pI-Phe       | Asp(Fm)      |                                    |
| 47 | pI-phe       | asp(Fm)      |                                    |
| 48 | Tyr(Me)      | pI-Phe       |                                    |
| 49 | tyr(Me)      | pI-phe       |                                    |
| 50 |              | Tyr(Me)      |                                    |
| 51 |              | tyr(Me)      |                                    |

*lower case lettering indicates D-amino acids

Pools of libraries were prepared in the positional scan format. A typical procedure for the combinatorial synthesis of the subject bicyclic guanidine combinatorial library was as follows. One hundred mg of p-methylbenzhydrylamine (MBHA) resin (0.81 meq/g, 100–200 mesh) was contained within a sealed polypropylene mesh packet. Following neutralization with 5% diisopropylethylamine (DIEA) in dichloromethane (DCM), the resin was washed with DCM. The first amino acid, which was Boc-protected, (6×) was coupled using the conventional reagents hydroxybenzotriazole (HOBt)(6×) and diisopropylcarbodiimide (DICI) (6×) (0.1 M final concentration in DMF) using the predetermined rates set forth above ([Boc-Xaa-OH] generating the $R^1$ group, as shown in FIG. 1). Following removal of the protecting group with 55% trifluoroacetic acid (TFA) in DCM, the packet was washed, neutralized and the second amino acid, which also was Boc-protected, was coupled again under the same conditions using the above predetermined rates ([Boc-Xaa-OH] generating the $R^2$ group, as shown in FIG. 1). Following removal of the Boc group, the dipeptide was individually acylated with a carboxylic acid in the presence of diisopropylcarbodiimide (DICI) and 1-hydroxybenzotriazole (HOBt) utilizing the above predetermined residues once again.

The reductions were performed in 50 ml kimax tubes under nitrogen. Boric acid (40×) and trimethyl borate (40×) were added, followed by 1M BH₃-THF (40×) The tubes were heated at 65° C. for 72 h, followed by quenching with MeOH. The resin was then washed with tetrahydrofuran and methanol. The amine-borane complex was disassociated by overnight treatment with piperidine at 65° C.

The cyclization occurred following treatment of the reduced acylated dipeptide with thiocarbonyldiimidazole (0.5 M in anhydrous dichloromethane) for 15 minutes followed by decantation of the solution, addition of anhydrous DCM, followed by shaking for 16 hours. This cyclization procedure was then repeated to ensure completion. Following cleavage from the resin with anhydrous HF by the procedures of Houghten et al. *Int. J. Pep. Prot. Res.,* 27:673 (1986), which is incorporated herein by reference, in the presence of anisole, the desired products were extracted and lyophilized.

EXAMPLE II

This example provides the synthesis of a combinatorial library of the present invention according to Reaction Scheme II, which is shown in FIG. 2. The $R^1$, $R^2$, $R^3$ and $R^4$ groups varied as described above and below. Again, thirty-four first amino acids were used, generating at least thirty-four $R^1$ groups, depending on the modifications to the side chains. The amino acids used to generate the $R^1$ groups are again listed in Table 5. Thirty-four second amino acids and seventeen third amino acids were used to generate the various respective $R^2$ and $R^3$ groups, which amino acids are again listed in Table 5. Finally, the seventy-one carboxylic acids used to acylate the tripeptides and generate the various $R^4$ groups are also listed again in Table 5. Therefore, Table 5 provides a summary of all the amino acids ($R^1$, $R^2$ and $R^3$) and carboxylic acids ($R^4$) used in the preparation of the combinatorial library.

TABLE 5

SUMMARY OF REAGENTS USED TO GENERATE R GROUPS IN PREPARED LIBRARIES

|   | R1  | R2  | R3   | R4                              |
|---|-----|-----|------|---------------------------------|
| 1 | Ala | Ala | Ala  | 1-phenyl-1-cyclopropyl carboxylic acid |
| 2 | Phe | Phe | Phe  | 2-phenylbutyric acid            |
| 3 | Ile | Ile | Gly  | 3-phenylbutyric acid            |
| 4 | Leu | Leu | Leu  | m-toluylacetic acid             |
| 5 | Val | Val | ala* | 3-fluorophenyl-acetic acid      |

TABLE 5-continued

SUMMARY OF REAGENTS USED TO GENERATE R GROUPS IN PREPARED LIBRARIES

| | R1 | R2 | R3 | R4 |
|---|---|---|---|---|
| 6 | Tyr(2BrZ) | Tyr(2BrZ) | phe | 3-bromophenylacetic acid |
| 7 | ala* | ala* | leu | (α,α,α-trifluoro-m-toluyl) acetic acid |
| 8 | phe | phe | Nva | p-toluylacetic acid |
| 9 | ile | ile | nva | 3-methoxyphenyl-acetic acid |
| 10 | leu | leu | Nle | 4-bromophenylacetic acid |
| 11 | val | val | nle | 4-methoxyphenyl-acetic acid |
| 12 | tyr(2BrZ) | tyr(2BrZ) | Cha | 4-ethoxyphenyl-acetic acid |
| 13 | alpha-Abu | alpha-Abu | cha | 4-isobutyl-α-methylphenyl-acetic acid |
| 14 | Aib | Nva | Tyr(OEt) | 3,4-dichlorophenyl-acetic acid |
| 15 | Nva | nva | tyr(OEt) | 3-(3,4-dimethoxyphenyl)-propionic acid |
| 16 | nva | Nle | Tyr(OMe) | 4-biphenylacetic acid |
| 17 | Nle | nle | Boc-D-tyr(OMe) | α-methylcinnamic acid |
| 18 | nle | Nal | | 2-(trifluoromethyl) cinnamic acid |
| 19 | Nal | nal | | (3,4-dimethoxyphenyl)-acetic acid |
| 20 | nal | Cha | | 3,4-(methylenedioxy)-phenylacetic acid |
| 21 | Cha | cha | | 2-methoxycinnamic acid |
| 22 | cha | Met(O)$_2$ | | Benzoic acid |
| 23 | pF-Phe | pF-Phe | | 4-chlorocinnamic acid |
| 24 | pF-phe | pF-phe | | m-anisic acid |
| 25 | pCl-Phe | pCl-Phe | | 4-isopropylbenzoic acid |
| 26 | pCl-phe | pCl-phe | | 4-vinylbenzoic acid |
| 27 | Chg | Chg | | 4-fluorobenzoic acid |
| 28 | chg | chg | | 4-bromobenzoic acid |
| 29 | Tyr(OEt) | Tyr(OEt) | | 3,4-dimethoxycinnamic acid |
| 30 | tyr(OEt) | tyr(OEt) | | t-cinnamic acid |
| 31 | pI-Phe | pI-Phe | | 3,4-dimethylbenzoic acid |
| 32 | pI-phe | pI-phe | | 3-fluoro-4-methylbenzoic acid |
| 33 | Tyr(OMe) | Tyr(OMe) | | 3-bromo-4-methylbenzoic acid |
| 34 | tyr(OMe) | tyr(OMe) | | 3-iodo-4-methylbenzoic acid |
| 35 | | | | 3,4-dichlorobenzoic acid |
| 36 | | | | 4-biphenyl-carboxylic acid |
| 37 | | | | 3,4-difluorobenzoic acid |
| 38 | | | | m-toluic acid |
| 39 | | | | phenylacetic acid |
| 40 | | | | hydrocinnamic acid |
| 41 | | | | 3-methoxy-4-methylbenzoic acid |
| 42 | | | | 4-phenylbutyric acid |
| 43 | | | | 3,4-dimethoxybenzoic acid |
| 44 | | | | 4-ethyl-4-biphenyl-carboxylic acid |
| 45 | | | | 3,4,5-trimethoxybenzoic acid |
| 46 | | | | butyric acid |
| 47 | | | | heptanoic acid |
| 48 | | | | isobutyric acid |
| 49 | | | | (+/-)-2-methylbutyric acid |
| 50 | | | | isovaleric acid |
| 51 | | | | 3-methylvaleric acid |
| 52 | | | | 4-methylvaleric acid |
| 53 | | | | p-toluic acid |
| 54 | | | | p-anisic acid |
| 55 | | | | cyclohexyl-carboxylic acid |
| 56 | | | | cyclohexylacetic acid |
| 57 | | | | cyclohexyl-butyric acid |
| 58 | | | | cycloheptane-carboxylic acid |
| 59 | | | | acetic acid |
| 60 | | | | 2-methyl-cyclopropane-carboxylic acid |
| 61 | | | | cyclobutane-carboxylic acid |
| 62 | | | | cyclopentane-carboxylic acid |
| 63 | | | | 3-cyclopentyl-propionic acid |
| 64 | | | | 2-furoic acid |
| 65 | | | | cyclohexyl-propionic acid |
| 66 | | | | 4-methyl-1-cyclohexyl-carboxylic acid |
| 67 | | | | 4-t-butylcyclohexyl-carboxylic acid |
| 68 | | | | 4-methylcyclohexyl acetic acid |
| 69 | | | | tiglic acid |
| 70 | | | | 2-norbornylacetic acid |
| 71 | | | | 2-thiophene-carboxylic acid |

*lower case lettering indicates D-amino acids

Pools of libraries were prepared in the positional scan format. A typical procedure for the combinatorial synthesis of the subject bicyclic guanidine combinatorial library was as follows. p-Methylbenzhydrylamine (MBHA) resin (100 mg, 0.81 meq/g, 100–200 mesh) was contained within a sealed polypropylene mesh packet. Following neutralization with 5% dissopropylethylamine (DIEA) in dichloromethane (DCM), the resin was washed with DCM. The first amino acid, which was Boc-protected, (6x) was coupled using the conventional reagents hydroxybenzotriazole (HOBt)(6x) and diisopropylcarbodiimide (DICI) (6x, 0.1 M final concentration in DMF) using the predetermined ratios set forth above, as necessary (generating the $R^1$ group, as shown in FIG. 2). Following removal of the Boc-protecting group with 55% trifluoroacetic acid (TFA) in DCM, the packet was washed, neutralized and the second amino acid, which also was Boc-protected, was coupled again under the same conditions using the above predetermined ratios, as necessary (generating the $R^2$ group, as shown in FIG. 2). Following removal of the Boc-protecting group of the second amino acid with 55% trifluoroacetic acid (TFA) in DCM, the packet was again washed, neutralized and the third amino acid, which also was Boc-protected, was coupled again under the same conditions using the above predetermined ratios, as necessary (generating the $R^3$ group, as shown in FIG. 2).

Following removal of the third Boc group, the tripeptide was reduced with borane ($BH_3$) in THF for four days. Specifically, the reductions were performed under nitrogen. Boric acid (40x) and trimethyl borate (40x) were added, followed by 1M $BH_3$-THF (40x). The resin was heated at 65° C. for 72 h, followed by quenching with MeOH. The resin was then washed with tetrahydrofuran and methanol. On the fourth day, the amine-borane complex was disassociated by overnight treatment with piperidine at 65° C.

Following the reduction, the N-terminus of the tripeptide was protected by a triphenylmethyl group by overnight treatment with a solution of 0.1M trityl chloride (5x) in DCM/DMF (9:1) in the presence of DIEA (25x). The three remaining secondary amines were then cyclized to form a bicyclic guanidine by treatment with 0.5M 1,1-thiocarbonyldiimidazole ($CSIm_2$) in anhydrous dichloromethane (DCM) twice for 16 hours.

The resin was then washed with DCM three times and the trityl chloride removed with 2% TFA. The free N-terminus of the guanidine was then acylated with a carboxylic acid in the presence of diisopropylcarbodiimide (DICI) and 1-hydroxybenzotriazole (HOBt) utilizing the above predetermined residues once again. To rid the guanidine of any HOBt salts and to encourage complete cyclization, the resin was treated with 20% piperidine in DMF for one hour and then four more times for five minutes each. Following final washings, the acylated bicyclic guanidine was treated with anhydrous HF for six hours to cleave it from the resin by the procedures of Houghten et al., Int. J. Pep. Prot. Res., 27:673 (1986), in the presence of anisole. The desired product was then extracted with 95% AcOH and lyophilized.

EXAMPLE III

Following the procedures of Example I, the following pools of libraries containing the bicyclic guanidines were prepared by the positional scan format according to the reaction scheme shown in FIG. 1. Therefore, the R groups and their respective pool reference numbers are identified in Table 6 below. Each of the 141 pools were screened in an anti-microbial assay, σ and κ-opioid receptor assays, as provided in Example IV, and in a CaMPDE assay, as provided in Examples IX to XI. In addition, pools were screened in an antifungal assay as provided in Example VII. This Example and Table 6 are provided for further reference for pool compositions in relation to the biological data in ensuing Examples IV, VII and IX to XI.

TABLE 6

LIBRARY POOL REFERENCE NUMBERS AND REAGENTS USED TO GENERATE VARIABLE R GROUPS FOR BICYCLIC GUANIDINE LIBRARY

| Pool No. | $R^1$ | $R^2$ | $R^3$ |
|---|---|---|---|
| 1 | X | X | 3-phenylbutyric acid |
| 2 | X | X | m-toluylacetic acid |
| 3 | X | X | 3-fluorophenylacetic acid |
| 4 | X | X | p-toluylacetic acid |
| 5 | X | X | 4-fluorophenylacetic acid |
| 6 | X | X | 3-methoxyphenylacetic acid |
| 7 | X | X | 4-methoxyphenylacetic acid |
| 8 | X | X | 4-ethoxyphenylacetic acid |
| 9 | X | X | 3-(3,4-dimethoxyphenyl)-propionic acid |
| 10 | X | X | 4-biphenylacetic acid |
| 11 | X | X | (3,4-dimethoxyphenyl)acetic acid |
| 12 | X | X | phenylacetic acid |
| 13 | X | X | hydrocinnamic acid |
| 14 | X | X | 4-phenylbutyric acid |
| 15 | X | X | butyric acid |
| 16 | X | X | heptanoic acid |
| 17 | X | X | isobutyric acid |
| 18 | X | X | (+/−)-2-methylbutyric acid |
| 19 | X | X | isovaleric acid |
| 20 | X | X | 3-methylvaleric acid |
| 21 | X | X | 4-methylvaleric acid |
| 22 | X | X | (tert-butyl)acetic acid |
| 23 | X | X | cyclohexylcarboxylic acid |
| 24 | X | X | cyclohexylacetic acid |
| 25 | X | X | cyclohexylbutyric acid |
| 26 | X | X | cycloheptanecarboxylic acid |
| 27 | X | X | lactic acid |
| 28 | X | X | acetic acid |
| 29 | X | X | cyclobutanecarboxylic acid |
| 30 | X | X | cyclopentanecarboxylic acid |
| 31 | X | X | 3-cyclopentylpropionic acid |
| 32 | X | X | cyclohexylpropionic acid |
| 33 | X | X | 4-methyl-1-cyclohexylcarboxylic acid |
| 34 | X | X | 4-(tert-butyl)cyclohexylcarboxylic acid |
| 35 | X | X | 2-norbornylacetic acid |
| 36 | X | X | 1-adamantaneacetic acid |
| 37 | X | X | 2-ethylbutyric |
| 38 | X | X | 3,3-diphenylpropionic acid |
| 39 | X | X | 2-methyl-4-nitro-1-imidazolepropionic acid |
| 40 | X | X | cyclopentylacetic acid |
| 41 | X | X | indole-3-acetic acid |
| 42 | X | Ala | X |
| 43 | X | Phe | X |
| 44 | X | Gly | X |
| 45 | X | Ile | X |
| 46 | X | Lys(Clz) | X |
| 47 | X | Leu | X |
| 48 | X | Met(O) | X |
| 49 | X | Arg(Tos) | X |
| 50 | X | Val | X |
| 51 | X | Tyr(Brz) | X |
| 52 | X | ala* | X |
| 53 | X | phe | X |
| 54 | X | ile | X |
| 55 | X | lys(Clz) | X |
| 56 | X | leu | X |
| 57 | X | arg(Tos) | X |
| 58 | X | val | X |

TABLE 6-continued

LIBRARY POOL REFERENCE NUMBERS AND REAGENTS USED TO GENERATE VARIABLE R GROUPS FOR BICYCLIC GUANIDINE LIBRARY

| Pool No. | $R^1$ | $R^2$ | $R^3$ |
|---|---|---|---|
| 59 | X | tyr(Brz) | X |
| 60 | X | α-Abu | X |
| 61 | X | Nve | X |
| 62 | X | nve | X |
| 63 | X | Nle | X |
| 64 | X | nle | X |
| 65 | X | Orn(Cbz) | X |
| 66 | X | Nap | X |
| 67 | X | nap | X |
| 68 | X | Cha | X |
| 69 | X | cha | X |
| 70 | X | Met(O$_2$) | X |
| 71 | X | pNO$_2$-Phe | X |
| 72 | X | pNO$_2$-phe | X |
| 73 | X | pCl-Phe | X |
| 74 | X | pCl-phe | X |
| 75 | X | pF-Phe | X |
| 76 | X | pF-phe | X |
| 77 | X | Lys(Ac) | X |
| 78 | X | Pya | X |
| 79 | X | pya | X |
| 80 | X | Chg | X |
| 81 | X | chg | X |
| 82 | X | tBu-Gly | X |
| 83 | X | pNH$_2$-Phe (Fmoc) | X |
| 84 | X | pNH$_2$-phe (Fmoc) | X |
| 85 | X | Tyr(Et) | X |
| 86 | X | tyr(Et) | X |
| 87 | X | Asp(Fm) | X |
| 88 | X | asp(Fm) | X |
| 89 | X | pI-Phe | X |
| 90 | X | pI-phe | X |
| 91 | X | Tyr(Me) | X |
| 92 | X | tyr(Me) | X |
| 93 | Ala | X | X |
| 94 | Phe | X | X |
| 95 | Ile | X | X |
| 96 | Lys(Clz) | X | X |
| 97 | Leu | X | X |
| 98 | Met(O) | X | X |
| 99 | Arg(Tos) | X | X |
| 100 | Val | X | X |
| 101 | Tyr(Brz) | X | X |
| 102 | ala* | X | X |
| 103 | phe | X | X |
| 104 | ile | X | X |
| 105 | lys(Clz) | X | X |
| 106 | leu | X | X |
| 107 | arg(Tos) | X | X |
| 108 | val | X | X |
| 109 | tyr(Brz) | X | X |
| 110 | α-Abu | X | X |
| 111 | α-Aib | X | X |
| 112 | Nve | X | X |
| 113 | nve | X | X |
| 114 | Nle | X | X |
| 115 | nle | X | X |
| 116 | Orn(Cbz) | X | X |
| 117 | Nap | X | X |
| 118 | nap | X | X |
| 119 | Cha | X | X |
| 120 | cha | X | X |
| 121 | Met(O$_2$) | X | X |
| 122 | pNO$_2$-Phe | X | X |
| 123 | pNO$_2$-phe | X | X |
| 124 | pCl-Phe | X | X |
| 125 | pCl-phe | X | X |
| 126 | pF-Phe | X | X |
| 127 | pF-phe | X | X |
| 128 | Lys(Ac) | X | X |
| 129 | Pya | X | X |
| 130 | pya | X | X |
| 131 | Chg | X | X |
| 132 | chg | X | X |
| 133 | tBu-Gly | X | X |
| 134 | pNH$_2$-Phe (Fmoc) | X | X |
| 135 | pNH2-phe (Fmoc) | X | X |
| 136 | Tyr(Et) | X | X |
| 137 | tyr(Et) | X | X |
| 138 | pI-Phe | X | X |
| 139 | pI-phe | X | X |
| 140 | Tyr(Me) | X | X |
| 141 | tyr(Me) | X | X |

*lower case lettering indicates D-amino acids

EXAMPLE IV

This example describes initial biological screens of all 141 combinatorial library pools as identified in the above Example III. More specifically, this example provides an initial screen of all the bicyclic guanidines in (1) the σ receptor assay and (3) κ-opioid receptor assay, each of which are described in detail above. The results of those screens are provided in Table 7 below. In addition, the results of the σ-receptor and κ-opioid receptor assays are depicted graphically in FIGS. 2 and 3.

The results of these assays evidence that many of the bicyclic guanidine compounds contained within the libraries are biologically active, as inhibitor of a specific receptors. Moreover, the results of the screens provide evidence that there is selectivity of certain compounds for one receptor over another.

TABLE 7

Radio-Receptor Assays Of The Bicyclic Guanidine Library (Positional Scanning Format)

| Pool No. | σ Receptor Assay (% Bound) | κ-Opioid Receptor Assay (% Bound) |
|---|---|---|
| 1 | 51.15 | 38.63 |
| 2 | 53.21 | 36.77 |
| 3 | 64.00 | 89.29 |
| 4 | 70.19 | 22.10 |
| 5 | 61.49 | 33.13 |
| 6 | 72.31 | 24.68 |
| 7 | 60.94 | 24.52 |
| 8 | 66.83 | 33.37 |
| 9 | 103.06 | 42.31 |
| 10 | 82.59 | 46.42 |
| 11 | 115.47 | 65.74 |
| 12 | 68.90 | 39.16 |
| 13 | 42.31 | 25.43 |
| 14 | 27.38 | 30.55 |
| 15 | 55.39 | 37.80 |
| 16 | 33.19 | 30.12 |
| 17 | 69.62 | 19.29 |
| 18 | 58.76 | 23.29 |
| 19 | 36.43 | 33.03 |
| 20 | 20.40 | 27.43 |

TABLE 7-continued

Radio-Receptor Assays Of The Bicyclic Guanidine Library (Positional Scanning Format)

| Pool No. | σ Receptor Assay (% Bound) | κ-Opioid Receptor Assay (% Bound) |
|---|---|---|
| 21 | 25.17 | 25.38 |
| 22 | 19.00 | 17.06 |
| 23 | 26.44 | 21.98 |
| 24 | 13.46 | 10.35 |
| 25 | 8.77 | 8.38 |
| 26 | 21.79 | 11.87 |
| 27 | 97.95 | 49.99 |
| 28 | 50.31 | 29.67 |
| 29 | 58.83 | 17.50 |
| 30 | 38.62 | 16.12 |
| 31 | 16.57 | 7.10 |
| 32 | 10.57 | 4.68 |
| 33 | 26.00 | 18.96 |
| 34 | 17.63 | 22.53 |
| 35 | 11.98 | 13.36 |
| 36 | 15.35 | 7.56 |
| 37 | 41.34 | 15.87 |
| 38 | 90.79 | 41.08 |
| 39 | 99.47 | 37.47 |
| 40 | 17.82 | 27.02 |
| 41 | 108.67 | 39.85 |
| 42 | 8.95 | 17.02 |
| 43 | 59.03 | 26.56 |
| 44 | 5.78 | 28.79 |
| 45 | 65.43 | 15.41 |
| 46 | 88.96 | 46.32 |
| 47 | 67.95 | 27.56 |
| 48 | 80.10 | 41.32 |
| 49 | 36.84 | 41.08 |
| 50 | 10.47 | 26.58 |
| 51 | 64.10 | 29.36 |
| 52 | 6.91 | 40.91 |
| 53 | 77.93 | 31.14 |
| 54 | 95.74 | 22.03 |
| 55 | 71.63 | 44.87 |
| 56 | 93.75 | 14.61 |
| 57 | 116.01 | 44.73 |
| 58 | 23.86 | 20.25 |
| 59 | 96.76 | 20.25 |
| 60 | 17.11 | 21.21 |
| 61 | 29.32 | 23.06 |
| 62 | 33.70 | 14.86 |
| 63 | 69.11 | 27.90 |
| 64 | 61.28 | 15.98 |
| 65 | 115.70 | 47.10 |
| 66 | 84.81 | 31.32 |
| 67 | 78.50 | 23.64 |
| 68 | 86.83 | 36.61 |
| 69 | 88.92 | 34.13 |
| 70 | 116.29 | 72.27 |
| 71 | 104.24 | 67.83 |
| 72 | 92.44 | 47.61 |
| 73 | 66.94 | 37.28 |
| 74 | 66.45 | 24.39 |
| 75 | 71.45 | 34.77 |
| 76 | 73.67 | 35.31 |
| 77 | 99.72 | 48.10 |
| 78 | 94.78 | 44.88 |
| 79 | 86.51 | 30.66 |
| 80 | 102.50 | 9.99 |
| 81 | 77.20 | 21.18 |
| 82 | 86.61 | 17.25 |
| 83 | 110.16 | 33.32 |
| 84 | 102.04 | 34.70 |
| 85 | 66.37 | 41.40 |
| 86 | 73.28 | 20.55 |
| 87 | 104.54 | 76.93 |
| 88 | 89.65 | 53.16 |
| 89 | 73.05 | 45.38 |
| 90 | 58.13 | 26.33 |
| 91 | 42.42 | 9.81 |
| 92 | 52.95 | 13.60 |
| 93 | 26.12 | 2.03 |
| 94 | 11.98 | 22.25 |
| 95 | 15.29 | 15.87 |
| 96 | 47.37 | 37.78 |
| 97 | 9.41 | 12.18 |
| 98 | 23.82 | 28.10 |
| 99 | 43.85 | 54.16 |
| 100 | 13.53 | 17.10 |
| 101 | 27.49 | 18.58 |
| 102 | 24.85 | 33.32 |
| 103 | 17.22 | 22.96 |
| 104 | 16.44 | 13.52 |
| 105 | 42.29 | 48.41 |
| 106 | 9.91 | 19.25 |
| 107 | 38.54 | 66.20 |
| 108 | 19.28 | 16.46 |
| 109 | 28.96 | 24.20 |
| 110 | 22.18 | 4.65 |
| 111 | 28.75 | 26.69 |
| 112 | 12.66 | 12.28 |
| 113 | 17.32 | 24.68 |
| 114 | 6.84 | 14.29 |
| 115 | 7.26 | 18.39 |
| 116 | 56.84 | 43.12 |
| 117 | 25.88 | 47.86 |
| 118 | 26.73 | 44.37 |
| 119 | 6.41 | 18.78 |
| 120 | 6.70 | 5.38 |
| 121 | 64.65 | 89.42 |
| 122 | 36.72 | 63.14 |
| 123 | 35.57 | 64.93 |
| 124 | 27.67 | 56.90 |
| 125 | 36.13 | 57.95 |
| 126 | 34.41 | 32.00 |
| 127 | 25.09 | 39.06 |
| 128 | 93.55 | 40.86 |
| 129 | 89.78 | 56.15 |
| 130 | 82.81 | 38.00 |
| 131 | 12.55 | 5.61 |
| 132 | 24.16 | 0.51 |
| 133 | 84.38 | 50.78 |
| 134 | 120.65 | 53.21 |
| 135 | 118.48 | 38.12 |
| 136 | 62.93 | 38.52 |
| 137 | 57.04 | 37.86 |
| 138 | 57.38 | 67.66 |
| 139 | 49.87 | 59.78 |
| 140 | 44.99 | 39.33 |
| 141 | 40.48 | 26.56 |

EXAMPLE V

From the above initial biological screens of all 141 combinatorial library pools, twenty-four individual compounds were synthesized separately and retested in the same assays to determine $IC_{50}$ values using similar conditions to those of Example I. The various $R^1$, $R^2$, and $R^3$ groups used in these individual synthesis are set forth below in Table 8. In summary, the twenty four individual compounds synthesized and tested were those compounds derived from every permutation of the following amino acids and carboxylic acids.

TABLE 8

SUMMARY OF R GROUPS FOR TWENTY-FOUR INDIVIDUAL COMPOUND S

| $R^1$ | $R^2$ | $R^3$ |
|---|---|---|
| Ala | O-Me-Tyr | cyclohexylpropionic acid |
| chg | O-Me-tyr* | 1-adamantaneacetic acid |
| Chg | leu | |
| | chg | |

*lower case lettering indicates D-amino acids

A typical procedure for the synthesis of an individual compound is as follows. One hundred mg of p-methylbenzhydrylamine (MBHA) resin (0.81 meq/g, 100–200 mesh) was contained within a sealed polypropylene mesh packet. Following neutralization with 5% diisopropylethylamine (DIEA) in dichloromethane (DCM), the resin was washed with DCM. The first amino acid coupled using the conventional reagents hydroxybenzotriazole (HOBt)(6×) and diisopropylcarbodiimide (DICI)(6×) (0.1 M final concentration in DMF). Following removal of the protecting group with 55% trifluoroacetic acid (TFA) in DCM, the packet was washed, neutralized and the second amino acid coupled under the same conditions as for the first amino acid. Following removal of the Boc group, the dipeptide was individually acylated with a carboxylic acid in the presence of diisopropylcarbodiimide (DICI) and 1-hydroxybenzotriazole (HOBt) under the same conditions as for the first amino acid.

Reduction was performed in a 50 ml kimax tube under nitrogen. Boric acid (40×) and trimethyl borate (40×) were added, followed by 1M $BH_3$-THF(40×). The tubes were heated at 65° C. for 72 h, followed by quenching with MeOH. The resin was then washed with tetrahydrofuran and methanol. The amine-borane complex was disassociated by overnight treatment with piperidine at 65° C.

Cyclization occurred following treatment of the reduced acylated dipeptide with thiocarbonyldiimidazole (0.5 M in dichloromethane anhydrous) for 15 minutes followed by decantation of the solution, addition of anhydrous DCM, followed by shaking for 16 hours. This cyclization procedure was repeated to ensure completion. Following cleavage from the resin with anhydrous HF by the procedures of Houghten et al. *Int. J. Pep. Prot. Res.*, 27:673 (1986), which is incorporated herein by reference, in the presence of anisole, the desired products were extracted and lyophilized. The desired product was obtained in good yield and purity following lyophilization.

The twenty-four individual bicyclic guanidine compounds were tested with: (1) the σ receptor assay; and (2) κ-opioid receptor assay, as described above. As provided in Tables 9 and 10, the results of these assays evidence that the individual compounds are inhibitors of the κ-opioid and σ receptors and have significant biologically activity. The compounds are provided below from most active to least active.

TABLE 9

K-OPIOID RECEPTOR ASSAY FOR 24 INDIVIDUAL COMPOUNDS

| Cmpd. No. | $R^1$ | $R^2$ | $R^3$ | $IC_{50}$ (nM) |
|---|---|---|---|---|
| 1 | Ala | Tyr(Me) | cyclohexylpropionic acid | 37 |
| 16 | Ala | Tyr(Me) | adamantaneacetic acid | 238 |
| 17 | chg | Tyr(Me) | adamantaneacetic acid | 341 |
| 4 | Ala | Tyr(Me) | cyclohexylpropionic acid | 502 |
| 5 | chg | Tyr(Me) | cyclohexylpropionic acid | 547 |
| 21 | Chg | leu | adamantaneacetic acid | 1206 |
| 24 | Chg | Chg | adamantaneacetic acid | 1492 |
| 13 | Ala | Tyr(Me) | adamantaneacetic acid | 1523 |
| 20 | chg | leu | adamantaneacetic acid | 1747 |
| 8 | chg | leu | cyclohexylpropionic acid | 1767 |
| 22 | Ala | Chg | adamantaneacetic acid | 1941 |
| 10 | Ala | Chg | cyclohexylpropionic acid | 2479 |
| 2 | chg | Tyr(Me) | cyclohexylpropionic acid | 3456 |
| 19 | Ala | leu | adamantaneacetic acid | 3641 |
| 9 | Chg | leu | cyclohexylpropionic acid | 3744 |
| 3 | Chg | Tyr(Me) | cyclohexylpropionic acid | 3872 |
| 12 | Chg | Chg | cyclohexylpropionic acid | 4482 |
| 15 | Chg | Tyr(Me) | adamantaneacetic acid | 4923 |
| 6 | Chg | Tyr(Me) | cyclohexylpropionic acid | 5026 |
| 7 | Ala | leu | cyclohexylpropionic acid | 5436 |
| 11 | chg | Chg | cyclohexylpropionic acid | 10333 |
| 18 | Chg | Tyr(Me) | adamantaneacetic acid | >10333 |
| 14 | chg | Tyr(Me) | adamantaneacetic acid | >10333 |
| 23 | chg | Chg | adamantaneacetic acid | >10333 |

TABLE 10

σ-RECEPTOR ASSAY FOR 24 INDIVIDUAL COMPOUNDS

| Cmpd. No. | $R^1$ | $R^2$ | $R^3$ | $IC_{50}$ (nM) |
|---|---|---|---|---|
| 9 | Chg | leu | cyclohexylpropionic acid | 13 |
| 3 | Chg | Tyr(Me) | cyclohexylpropionic acid | 23 |
| 5 | chg | Tyr(Me) | cyclohexylpropionic acid | 42 |
| 4 | Ala | Tyr(Me) | cyclohexylpropionic acid | 52 |
| 17 | chg | Tyr(Me) | adamantaneacetic acid | 56 |
| 6 | Chg | Tyr(Me) | cyclohexylpropionic acid | 68 |
| 1 | Ala | Tyr(Me) | cyclohexylpropionic acid | 94 |
| 21 | Chg | leu | adamantaneacetic acid | 124 |
| 8 | chg | leu | cyclohexylpropionic acid | 201 |
| 12 | Chg | Chg | cyclohexylpropionic acid | 210 |
| 13 | Ala | Tyr(Me) | adamantaneacetic acid | 235 |
| 15 | Chg | Tyr(Me) | adamantaneacetic acid | 256 |
| 20 | chg | Leu | adamantaneacetic acid | 267 |
| 18 | Chg | Tyr(Me) | adamantaneacetic acid | 297 |
| 10 | Ala | Chg | cyclohexylpropionic acid | 348 |
| 11 | Chg | Chg | cyclohexylpropionic acid | 405 |
| 7 | Ala | leu | cyclohexylpropionic acid | 530 |
| 2 | chg | Tyr(Me) | cyclohexylpropionic acid | 585 |
| 14 | chg | Tyr(Me) | adamantaneacetic acid | 823 |
| 24 | Chg | Chg | adamantaneacetic acid | 930 |
| 19 | Ala | leu | adamantaneacetic acid | 974 |
| 22 | Ala | Chg | adamantaneacetic acid | 1025 |
| 16 | Ala | Tyr(Me) | adamantaneacetic acid | 1077 |
| 23 | chg | Chg | adamantaneacetic acid | 1577 |

EXAMPLE VI

An additional seventeen individual compounds were synthesized and tested for activity in the σ-receptor assay. The individual compounds were synthesized following the same procedures as provided above in Example V and using the amino acids and carboxylic acids listed in Table 11 below. The $IC_{50}$ values were determined as detailed above. The results provided in Table 11 below evidence the significant biological activity of the compounds.

TABLE 11

σ-RECEPTOR ASSAY FOR 17 INDIVIDUAL COMPOUNDS

| $R^1$ | $R^2$ | $R^3$ | $IC_{50}$(nM) |
|---|---|---|---|
| Phe | Nal | acetic acid | 22 |
| Phe | Tyr(Et) | acetic acid | 33 |
| Phe | nal | acetic acid | 42 |
| Phe | Cha | acetic acid | 52 |
| Phe | pCl-Phe | acetic acid | 60 |
| Phe | Tyr(Et) | acetic acid | 64 |
| Phe | pI-Phe | acetic acid | 65 |
| Phe | Tyr(Me) | acetic acid | 69 |
| Phe | pNO$_2$-Phe | acetic acid | 102 |
| Phe | Phe | (tert-butyl)acetic acid | 112 |
| Phe | chg | acetic acid | 119 |
| Phe | pCl-phe | acetic acid | 127 |
| Phe | Phe | isovaleric acid | 156 |
| Phe | Lys(Ac) | acetic acid | 202 |
| Nle | Phe | acetic acid | 214 |
| Phe | pF-Phe | acetic acid | 215 |
| Phe | pF-phe | acetic acid | 242 |

EXAMPLE VII

This example describes initial antifungal screens of combinatorial library pools identified in Example III. In addition, the results of the antifungal assay is depicted in FIG. 5. The results of this assay evidences that many of the bicyclic guanidine compounds contained within the libraries are biologically active as antifungal agents.

TABLE 12

Anti-Fungal Assay of a Bicyclic Guanidine Library

| Pool No. | $IC_{50}$(μg/ml) | MIC(μg/ml) |
|---|---|---|
| 119 | 18 | 20–32 |
| 120 | 19 | 25–32 |
| 132 | 34 | 40–62 |
| 131 | 37 | 45–62 |
| 126 | 94 | >250 |
| 127 | 97 | 125–250 |
| 115 | 105 | >250 |
| 128 | 145 | >250 |
| 112 | 161 | >250 |
| 95 | 170 | >250 |
| 96 | 172 | >250 |
| 113 | 176 | >250 |
| 97 | 176 | >250 |
| 111 | 180 | >250 |
| 106 | 181 | 200–250 |
| 103 | 182 | >250 |
| 124 | 182 | >250 |
| 104 | 185 | 200–250 |
| 141 | 188 | >250 |
| 108 | 194 | >250 |
| 125 | 195 | >250 |
| 98 | 197 | 250 |
| 136 | 199 | >250 |
| 116 | 199 | >250 |
| 100 | 200 | >250 |
| 105 | 206 | >250 |
| 94 | 229 | >250 |
| 134 | 236 | >250 |
| 135 | 240 | >250 |
| other | >250 | >250 |
| pools | | |
| 68 | 20 | 32–62 |
| 69 | 23 | 32–62 |
| 80 | 48 | 70–125 |
| 81 | 78 | 125–250 |
| 54 | 80 | 125–250 |
| 74 | 88 | >250 |
| 44 | 138 | 150–250 |
| 56 | 169 | >250 |
| 47 | 172 | >250 |
| 85 | 175 | >250 |
| 64 | 177 | >250 |
| 86 | 181 | >250 |
| 63 | 182 | >250 |
| 73 | 182 | >250 |
| 58 | 185 | >250 |
| 61 | 187 | >250 |
| 43 | 189 | >250 |
| 82 | 191 | >250 |
| 83 | 193 | >250 |
| 62 | 201 | >250 |
| 91 | 201 | >250 |
| 84 | 208 | >250 |
| 45 | 210 | >250 |
| 53 | 211 | >250 |
| 75 | 211 | >250 |
| 74 | 215 | >250 |
| 72 | 224 | >250 |
| 89 | 225 | >250 |
| other pools | >250 | >250 |
| 34 | 19 | 32–62 |
| 36 | 22 | 32–64 |
| 25 | 40 | 50–62 |
| 35 | 54 | 125–250 |
| 16 | 80 | 125–250 |
| 31 | 80 | 125–250 |
| 31 | 80 | 125–250 |
| 33 | 82 | 125–250 |
| 24 | 85 | 125–250 |
| 32 | 100 | 200–250 |
| 20 | 119 | >250 |
| 21 | 121 | >250 |
| 26 | 142 | >250 |
| 13 | 144 | >250 |
| 40 | 155 | >250 |
| 22 | 202 | >250 |
| 14 | 203 | >250 |
| 23 | 208 | >250 |
| 37 | 214 | >250 |
| 30 | 218 | >250 |
| 1 | 220 | >250 |
| 4 | 227 | >250 |
| 3 | 229 | >250 |
| 6 | 234 | >250 |
| other pools | >250 | >250 |

EXAMPLE VIII

From the above initial screens of all 141 combinatorial library pools, thirty-two individual compounds were synthesized separately under procedures similar to those described in Example V. These compounds were retested in the same antifungal assay to determine $IC_{50}$ and MIC values as set forth below in Table 13. The various R groups used are also set forth in Table 13.

TABLE 13

Anti-Fungal Activity Assay for 32 Individual Compounds

| R¹ | R² | R³ | IC$_{50}$(μg/ml) | MIC(μg/ml) |
|---|---|---|---|---|
| cha | Cha | 4-(tert-butyl)-cyclohexyl-carboxylic acid | 2.34 | 3–4 |
| chg | Cha | 1-adamantaneacetic acid | 2.40 | 3–4 |
| Chg | cha | 1-adamantaneacetic acid | 2.52 | 3–4 |
| cha | Cha | 1-adamantaneacetic acid | 2.92 | 4–8 |
| Cha | cha | 1-adamantaneacetic acid | 3.00 | 4–8 |
| chg | Cha | 4-(tert-butyl)-cyclohexyl-carboxylic acid | 3.53 | 4–8 |
| Cha | Cha | 4-(tert-butyl)-cyclohexyl-carboxylic acid | 4.22 | 5–8 |
| Cha | cha | 4-(tert-butyl)-cyclohexyl-carboxylic acid | 4.39 | 5–8 |
| Cha | Cha | 1-adamantaneacetic acid | 4.42 | 5–8 |
| cha | cha | 4-(tert-butyl)-cyclohexyl-carboxylic acid | 4.54 | 5–8 |
| Chg | cha | 4-(tert-butyl)-cyclohexyl-carboxylic acid | 4.57 | 5–8 |
| chg | cha | 4-(tert-butyl)-cyclohexyl-carboxylic acid | 6.61 | 8–16 |
| cha | cha | 1-adamantaneacetic acid | 7.29 | 8–16 |
| Cha | Chg | 4-(tert-butyl)-cyclohexyl-carboxylic acid | 7.31 | 8–16 |
| cha | Chg | 1-adamantaneacetic acid | 8.27 | 10–16 |
| Chg | Cha | 4-(tert-butyl)-cyclohexyl-carboxylic acid | 8.71 | 10–16 |
| cha | chg | 4-(tert-butyl)-cyclohexyl-carboxylic acid | 8.75 | 10–16 |
| chg | Chg | 1-adamantaneacetic acid | 9.01 | 10–16 |
| cha | chg | 1-adamantaneacetic acid | 9.12 | 10–16 |
| Cha | chg | 4-(tert-butyl)-cyclohexyl-carboxylic acid | 9.19 | 10–16 |
| Cha | Chg | 1-adamantaneacetic acid | 9.29 | 10–16 |
| Cha | chg | 1-adamantaneacetic acid | 9.36 | 10–16 |
| cha | Chg | 4-(tert-butyl)-cyclohexyl-carboxylic acid | 9.67 | 16–32 |
| Chg | chg | 1-adamantaneacetic acid | 9.92 | 11–16 |
| chg | Chg | 4-(tert-butyl)-cyclohexyl-carboxylic acid | 16.80 | 18–32 |
| Chg | Chg | 1-adamantaneacetic acid | 18.58 | 20–32 |
| chg | chg | 1-adamantaneacetic acid | 23.13 | 32–64 |
| chg | cha | 1-adamantaneacetic acid | 23.79 | 32–64 |
| Chg | Chg | 4-(tert-butyl)-cyclohexyl-carboxylic acid | 24.07 | 32–64 |
| Chg | chg | 4-(tert-butyl)-cyclohexyl-carboxylic acid | 29.34 | >62 |
| chg | chg | 4-(tert-butyl)-cyclohexyl-carboxylic acid | 34.28 | >62 |
| Chg | Cha | 1-adamantaneacetic acid | 38.77 | >62 |

*lower case indicates D-amino acid

EXAMPLE IX

This example describes initial screens of all 141 combinatorial library pools identified in Example III for activity as calmodulin antagonists. The results of the screens provided in Table 14 below. In addition, the results of the CaMPDE assay is depicted in FIG. 6. The results of this assay evidences that many of the bicyclic guanidine compounds contained within the libraries are biologically active as calmodulin antagonists.

TABLE 14

CaMPDE Assay of a Bicyclic Guanidine Library (Positional Scanning Format)

| Pool No. | % Inhibition |
|---|---|
| 117 | ≧100 |
| 118 | ≧100 |
| 138 | ≧100 |
| 126 | ≧100 |
| 125 | ≧100 |
| 107 | ≧100 |
| 139 | ≧100 |
| 127 | 99.6 |
| 122 | 97.2 |
| 123 | 94.6 |
| 119 | 91.9 |
| 135 | 86.7 |
| 124 | 85.9 |
| 94 | 82.3 |
| 134 | 78.4 |
| 103 | 75.8 |
| 120 | 69.0 |
| 137 | 61.3 |
| 110 | 56.3 |
| 101 | 54.7 |
| 97 | 54.5 |
| 95 | 53.3 |
| 140 | 48.4 |
| 98 | 47.0 |
| 105 | 46.8 |
| 114 | 41.6 |
| 96 | 39.8 |
| 104 | 38.6 |
| 141 | 34.3 |
| 129 | 34.1 |
| 132 | 31.5 |
| 128 | 28.3 |
| 106 | 27.3 |
| 112 | 26.3 |
| 100 | 25.5 |
| 115 | 22.9 |
| 93 | 21.5 |
| 116 | 21.5 |
| 108 | 21.0 |
| 121 | 18.8 |
| 110 | 17.4 |
| 133 | 8.6 |
| 102 | 6.7 |
| 67 | ≧100 |
| 66 | ≧100 |

TABLE 14-continued

CaMPDE Assay of a Bicyclic Guanidine Library
(Positional Scanning Format)

| Pool No. | % Inhibition |
| --- | --- |
| 57 | ≧100 |
| 74 | ≧100 |
| 69 | ≧100 |
| 89 | ≧100 |
| 73 | ≧100 |
| 68 | ≧100 |
| 75 | ≧100 |
| 72 | ≧100 |
| 90 | 97.8 |
| 80 | 96.5 |
| 71 | 92.1 |
| 53 | 90.8 |
| 49 | 88.9 |
| 43 | 88.5 |
| 81 | 88.2 |
| 76 | 82.5 |
| 54 | 81.6 |
| 91 | 71.8 |
| 56 | 68.6 |
| 47 | 67.7 |
| 45 | 66.1 |
| 64 | 65.6 |
| 70 | 65.0 |
| 82 | 61.8 |
| 85 | 55.4 |
| 62 | 52.4 |
| 86 | 47.6 |
| 55 | 46.0 |
| 84 | 45.3 |
| 83 | 42.8 |
| 46 | 39.8 |
| 50 | 38.2 |
| 65 | 38.2 |
| 51 | 37.3 |
| 60 | 34.8 |
| 61 | 30.5 |
| 42 | 29.8 |
| 52 | 29.1 |
| 87 | 27.3 |
| 58 | 26.4 |
| 48 | 20.0 |
| 78 | 15.4 |
| 79 | 9.2 |
| 77 | 7.0 |
| 44 | 0 |
| 88 | 0 |
| 32 | ≧100 |
| 10 | ≧100 |
| 34 | ≧100 |
| 25 | ≧100 |
| 31 | ≧100 |
| 36 | ≧100 |
| 26 | ≧100 |
| 8 | ≧100 |
| 14 | ≧100 |
| 24 | ≧100 |
| 35 | ≧100 |
| 40 | ≧100 |
| 23 | 99.9 |
| 5 | 99.4 |
| 6 | 99.4 |
| 33 | 96.5 |
| 39 | 89.4 |
| 13 | 88.9 |
| 21 | 88.9 |
| 17 | 88.0 |
| 22 | 82.8 |
| 30 | 82.8 |
| 3 | 80.9 |
| 2 | 79.8 |
| 12 | 79.6 |
| 1 | 78.7 |
| 7 | 77.3 |
| 4 | 73.6 |

TABLE 14-continued

CaMPDE Assay of a Bicyclic Guanidine Library
(Positional Scanning Format)

| Pool No. | % Inhibition |
| --- | --- |
| 37 | 73.6 |
| 18 | 68.4 |
| 15 | 58.3 |
| 9 | 54.7 |
| 29 | 50.8 |
| 28 | 37.8 |
| 19 | 28.7 |

EXAMPLE X

After the initial screen, $IC_{50}$ values were determined for combinatorial library pools with the most activity. These results are provided in Table 15 below.

TABLE 15

CaMPDE Assay of a Bicyclic Guanidine Library
(Positional Scanning Format)
(Determination of $IC_{50}$ Values)

| Pool No. | $IC_{50}$ (µg/ml) |
| --- | --- |
| 126 | 5.0 |
| 138 | 5.3 |
| 118 | 5.3 |
| 136 | 6.4 |
| 99 | 8.3 |
| 134 | 8.8 |
| 120 | 9.1 |
| 117 | 9.1 |
| 131 | 9.4 |
| 135 | 9.7 |
| 103 | 10.6 |
| 139 | 10.6 |
| 123 | 10.9 |
| 107 | 11.1 |
| 137 | 11.3 |
| 127 | 11.3 |
| 119 | 11.9 |
| 94 | 12.2 |
| 111 | 12.5 |
| 97 | 12.8 |
| 95 | 13.3 |
| 101 | 14.7 |
| 66 | 3.9 |
| 67 | 4.7 |
| 89 | 4.7 |
| 75 | 5.8 |
| 49 | 7.0 |
| 43 | 8.4 |
| 68 | 8.7 |
| 69 | 8.8 |
| 82 | 9.0 |
| 81 | 9.2 |
| 84 | 9.3 |
| 80 | 10.2 |
| 57 | 10.3 |
| 74 | 10.4 |
| 64 | 11.6 |
| 53 | 11.8 |
| 76 | 11.9 |
| 83 | 12.1 |
| 56 | 12.2 |
| 54 | 12.3 |
| 45 | 12.8 |
| 92 | 14.4 |
| 85 | 14.6 |
| 62 | 16.1 |
| 70 | 17.6 |
| 59 | 17.9 |

TABLE 15-continued

CaMPDE Assay of a Bicyclic Guanidine Library
(Positional Scanning Format)
(Determination of IC$_{50}$ Values)

| Pool No. | IC$_{50}$ (μg/ml) |
|---|---|
| 47 | 18.0 |
| 63 | 26.4 |
| 32 | 3.1 |
| 10 | 3.4 |
| 38 | 4.9 |
| 34 | 5.0 |
| 25 | 5.3 |
| 13 | 7.2 |
| 3 | 7.8 |
| 36 | 7.9 |
| 35 | 8.0 |
| 6 | 8.1 |
| 37 | 8.6 |
| 41 | 9.2 |
| 26 | 10.1 |
| 16 | 10.2 |
| 5 | 10.2 |
| 4 | 10.4 |
| 8 | 10.5 |
| 1 | 10.7 |
| 23 | 10.9 |
| 24 | 10.9 |
| 33 | 11.2 |
| 21 | 11.4 |
| 40 | 12.0 |
| 30 | 12.1 |
| 22 | 12.2 |
| 39 | 12.2 |
| 7 | 13.3 |
| 20 | 13.4 |
| 18 | 14.3 |
| 15 | 14.5 |
| 11 | 15.8 |
| 29 | 16.8 |
| 27 | 18.5 |
| 9 | 19.0 |

EXAMPLE XI

The active mixtures listed in Table 15 above were also screened for specificity to calmodulin versus phosphodiesterase. These results are provided in Table 16 below.

TABLE 16

Specificity To CaM versus PDE of a Bicyclic Guanidine
Library at 15 μg/ml
(Positional Scanning Format)

| Pool No. | CaM (% inhibition) | PDE (% inhibition) | Specificity |
|---|---|---|---|
| 117 | 115.5 | 13.9 | 8.3 |
| 118 | 114.9 | 23.7 | 4.8 |
| 138 | 109.7 | 30.9 | 3.5 |
| 126 | 107.9 | 27.2 | 4.0 |
| 125 | 106.4 | 25.4 | 4.2 |
| 107 | 101.4 | 28.3 | 3.6 |
| 139 | 101.0 | 32.7 | 3.1 |
| 125 | 99.6 | 15.6 | 6.4 |
| 122 | 97.2 | 24.9 | 3.9 |
| 123 | 94.6 | 21.1 | 4.5 |
| 119 | 91.9 | 24.3 | 3.8 |
| 135 | 86.7 | 41.6 | 2.1 |
| 124 | 85.9 | 24.3 | 3.5 |
| 94 | 82.3 | 15.6 | 5.3 |
| 134 | 78.4 | 31.5 | 2.5 |
| 103 | 75.8 | 15.0 | 5.0 |
| 67 | 129.8 | 28.3 | 4.6 |
| 66 | 123.9 | 31.8 | 3.9 |
| 89 | 115.9 | 23.7 | 4.9 |
| 73 | 115.0 | 35.0 | 3.3 |
| 68 | 107.4 | 27.2 | 4.0 |
| 75 | 107.4 | 48.8 | 2.2 |
| 72 | 107.0 | 28.0 | 3.8 |
| 90 | 97.8 | 33.2 | 2.9 |
| 80 | 96.5 | 22.8 | 4.2 |
| 71 | 92.1 | 30.1 | 3.1 |
| 53 | 90.8 | 17.3 | 5.2 |
| 49 | 88.9 | 31.5 | 2.8 |
| 43 | 88.5 | 15.0 | 5.9 |
| 81 | 88.2 | 17.6 | 5.0 |
| 76 | 82.5 | 20.5 | 4.0 |
| 54 | 81.6 | 9.5 | 8.6 |
| 32 | 149.2 | 64.5 | 2.3 |
| 10 | 140.5 | 56.9 | 2.5 |
| 34 | 137.8 | 32.4 | 4.3 |
| 25 | 134.4 | 36.1 | 3.7 |
| 38 | 132.5 | 17.9 | 7.4 |
| 41 | 128.7 | 33.2 | 3.9 |
| 16 | 119.1 | 48.6 | 2.5 |
| 31 | 119.1 | 30.9 | 3.9 |
| 36 | 116.3 | 45.1 | 2.6 |
| 26 | 115.9 | 34.7 | 3.3 |
| 8 | 114.5 | 36.1 | 3.2 |
| 40 | 100.6 | 17.6 | 5.7 |
| 23 | 99.9 | 35.0 | 2.9 |
| 5 | 99.4 | 9.8 | 10.1 |
| 6 | 99.4 | 35.3 | 2.8 |
| 33 | 96.5 | 28.3 | 3.4 |
| 39 | 89.4 | 35.0 | 2.6 |
| 13 | 88.9 | 52.6 | 1.7 |
| 21 | 88.9 | 20.5 | 4.3 |
| 17 | 88.0 | 32.9 | 2.7 |
| 22 | 82.8 | 22.5 | 3.7 |
| 30 | 82.8 | 29.2 | 2.8 |
| 3 | 80.9 | 26.6 | 3.0 |
| 2 | 79.8 | 33.8 | 2.4 |
| 12 | 79.6 | 43.9 | 1.8 |
| 1 | 78.7 | 37.3 | 2.1 |
| 7 | 77.3 | 29.5 | 2.6 |
| 4 | 73.6 | 25.4 | 2.9 |
| 37 | 73.6 | 19.1 | 3.9 |

EXAMPLE XII

From the above screens, fifty-three individual compounds were assayed and their IC$_{50}$ values determined. These results, as well as each compounds R groups, are provided in Table 17 below.

TABLE 17

CaMPDE Assay for 53 Individual Compounds

| R$^1$ | R$^2$ | R$^3$ | IC$_{50}$ (μg/ml) |
|---|---|---|---|
| L-Cha | D-cha | 4-(tert-butyl)-cyclohexylcarboxylic acid | 0.86 |
| L-Cha | L-Cha | 4-(tert-butyl)-cyclohexylcarboxylic acid | 1.02 |
| L-Cha | D-cha | 1-adamantaneacetic acid | 1.05 |
| L-Chg | D-cha | 4-(tert-butyl)-cyclohexylcarboxylic acid | 1.06 |
| D-cha | L-Cha | 4-(tert-butyl)-cyclohexylcarboxylic acid | 1.28 |

TABLE 17-continued

CaMPDE Assay for 53 Individual Compounds

| R¹ | R² | R³ | IC$_{50}$ (μg/ml) |
|---|---|---|---|
| L-Chg | D-cha | 1-adamantaneacetic acid | 1.28 |
| D-chg | L-Cha | 4-(tert-butyl)-cyclohexylcarboxylic acid | 1.41 |
| L-Cha | D-chg | 4-(tert-butyl)-cyclohexylcarboxylic acid | 1.76 |
| D-cha | L-Cha | 1-adamantaneacetic acid | 1.85 |
| L-Chg | D-chg | 1-adamantaneacetic acid | 2.02 |
| D-cha | D-cha | 4-(tert-butyl)-cyclohexylcarboxylic acid | 2.02 |
| D-cha | L-Chg | 4-(tert-butyl)-cyclohexylcarboxylic acid | 2.08 |
| D-cha | D-chg | 4-(tert-butyl)-cyclohexylcarboxylic acid | 2.09 |
| D-chg | L-Cha | 1-adamantaneacetic acid | 2.14 |
| L-Chg | L-Cha | 4-(tert-butyl)-cyclohexylcarboxylic acid | 2.30 |
| L-Cha | D-chg | 1-adamantaneacetic acid | 2.76 |
| D-chg | L-Cha | 1-adamantaneacetic acid | 2.92 |
| L-Phe | L-Phe | cyclohexylbutyric acid | 3.00 |
| L-Cha | L-Cha | 1-adamantaneacetic acid | 3.66 |
| D-chg | D-cha | 4-(tert-butyl)-cyclohexylcarboxylic acid | 3.82 |
| L-Cha | L-Chg | 4-(tert-butyl)-cyclohexylcarboxylic acid | 4.45 |
| D-cha | L-Chg | 1-adamantaneacetic acid | 4.57 |
| D-chg | L-Chg | 4-(tert-butyl)-cyclohexylcarboxylic acid | 4.58 |
| D-cha | D-cha | 1-adamantaneacetic acid | 4.75 |
| L-Phe | L-Asp(Fm) | acetic acid | 5.48 |
| L-Chg | D-chg | 4-(tert-butyl)-cyclohexylcarboxylic acid | 5.61 |
| D-chg | L-Chg | 1-adamantaneacetic acid | 5.66 |
| L-Chg | O-tyr(Me) | cyclohexylpropionic acid | 5.77 |
| L-Phe | L-Phe | 2,4-dinitrophenylacetic acid | 6.06 |
| L-Chg | L-Cha | 1-adamantaneacetic acid | 6.07 |
| L-Chg | O-tyr(Me) | 1-adamantaneacetic acid | 6.21 |
| L-Chg | L-Chg | 4-(tert-butyl)-cyclohexylcarboxylic acid | 6.25 |
| D-chg | O-tyr(Me) | cyclohexylpropionic acid | 6.28 |
| D-chg | L-Cha | cyclohexylpropionic acid | 6.48 |
| D-chg | D-chg | 4-(tert-butyl)-cyclohexylcarboxylic acid | 6.61 |
| L-Phe | L-Phe | 4-biphenylacetic acid | 6.65 |
| D-chg | D-cha | 1-adamantaneacetic acid | 6.80 |
| D-chg | O-Tyr(Me) | cyclohexylpropionic acid | 6.92 |
| L-Chg | D-leu | 1-adamantaneacetic acid | 6.96 |
| L-Phe | D-trp | acetic acid | 7.00 |
| L-Cha | L-Chg | 1-adamantaneacetic acid | 7.32 |
| L-Phe | L-Phe | 1-adamantaneacetic acid | 7.56 |
| D-cha | D-chg | 1-adamantaneacetic acid | 7.85 |
| L-Chg | L-Chg | 1-adamantaneacetic acid | 8.65 |
| L-Phe | L-Trp | acetic acid | 8.88 |
| L-Phe | L-Phe | cyclohexylpropionic acid | 8.93 |
| D-chg | D-chg | 1-adamantaneacetic acid | 9.39 |
| L-Chg | D-leu | cyclohexylpropionic acid | 9.41 |
| L-Phe | L-Phe | 4-(tert-butyl)-cyclohexylcarboxylic acid | 9.53 |
| D-ala | L-Phe | acetic acid | 9.75 |
| L-Met(O) | L-Phe | acetic acid | 9.79 |
| L-Formyl-Trp | L-Phe | acetic acid | 10.70 |
| L-Chg | L-Cha | 1-adamantaneacetic acid | 11.66 |

All journal article and reference citations provided above, in parentheses or otherwise, whether previously stated or not, are incorporated herein by reference.

Although the invention has been described with reference to the examples provided above, it should be understood that various modifications can be made without departing from the spirit of the inventions. Accordingly the invention is limited only by the claims.

We claim:

1. A single bicyclic guanidine compound of the structure:

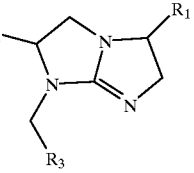

wherein:

R¹ is selected from the groups consisting of $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, and substituted benzyl;

R² is selected from the groups consisting of $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, substituted benzyl, naphthyl, and substituted naphthyl; and R³ is selected from the group consisting of a hydrogen atom, $C_1$ to $C_{10}$ alkyl, $C_2$ to $C_{10}$ alkenyl, $C_1$ to $C_{10}$ substituted alkyl, $C_2$ to $C_{10}$ alkynyl, $C_3$ to $C_7$ substituted cycloalkyl, $C_3$ to $C_7$ cycloalkenyl, $C_3$ to $C_7$ substituted cycloalkenyl, $C_7$ to $C_{16}$ phenylalkyl, $C_7$ to $C_{16}$ substituted phenylalkyl, $C_7$ to $C_{16}$ phenylalkenyl and $C_7$ to $C_{16}$ substituted phenylalkenyl;

or a pharmaceutically-acceptable salt thereof.

2. A single bicyclic guanidine compound of the structure:

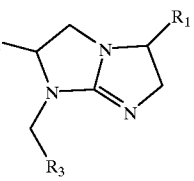

wherein:

R¹ is selected from the group consisting of methyl, benzyl, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, dimethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, 4-iodobenzyl, 4-methoxybenzyl and N-(methyl)indol-3-ylmethyl;

R² is selected from the group consisting of methyl, benzyl, hydrogen, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, hydroxyethyl, 4-iodobenzyl, 4-methoxybenzyl and indol-3-ylmethyl; and $R^3$ is selected from the group consisting of 3-phenylbutyl, m-toluylethyl, 3-fluorophenylethyl, p-toluylethyl, 4-fluorophenylethyl, 3-methoxyphenylethyl, 4-methoxyphenylethyl, 4-ethoxyphenylethyl, 3-(3,4-dimethoxyphenyl)propyl, 4-biphenylethyl, 3,4-dimethoxyphenylethyl, phenylethyl, 3-phenylpropyl, 4-phenylbutyl, butyl, heptyl, isobutyryl, (+/-)-2-methylbutyl, isovaleryl, 3-methylvaleryl, 4-methylvaleryl, (tert-butyl)ethyl, cyclohexylmethyl, cyclohexylethyl, cyclohexylbutyl, cycloheptylmethyl, 2-hydroxypropyl, ethyl, cyclobutylmethyl, cyclopentylmethyl, 3-cyclopentylpropyl, cyclohexylpropyl, 4-methyl-1-cyclohexylmethyl, 4-(tert-butyl)-1-cyclohexylmethyl, 2-norbornylethyl, 1-adamantylethyl, 2-ethylbutyl, 3,3-diphenylpropyl, 2-methyl-4-nitro-1-imidazolylpropyl, cyclopentylethyl, 3-indolylethyl and 2,4-dinitrophenylethyl.

3. The compound of claim 1, wherein:
$R^1$ is selected from the group consisting of methyl and cyclohexyl;
$R^2$ is selected from the group consisting of 4-methoxybenzyl, 2-methylpropyl and cyclohexyl; and
$R^3$ is selected from the group consisting of 3-cyclohexylpropyl and 1-adamantylethyl.

4. The compound of claim 1, wherein:
$R^1$ is selected from the group consisting of benzyl and butyl;
$R^2$ is selected from the group consisting of 2-naphthylmethyl, 4-ethoxybenzyl, cyclohexylmethyl, 4-chlorobenzyl, 4-iodobenzyl, 4-methoxybenzyl, 4-nitrobenzyl, benzyl, cyclohexyl, N-ethyl,N-thiocarbonylimidazole-aminobutyl, and 4-fluorobenzyl; and
$R^3$ is selected from the group consisting of methyl, (tert-butyl)ethyl and isovaleryl.

5. The compound of claim 1, wherein:
$R^1$ is selected from the group consisting of cyclohexyl and cyclohexylmethyl;
$R^2$ is selected from the group consisting of cyclohexyl and cyclohexylmethyl; and
$R^3$ is selected from the group consisting of 4-tert-butyl-1-cyclohexylmethyl and 1-adamantylethyl.

6. The compound of claim 1, wherein:
$R^1$ is selected from the group consisting of cyclohexyl, cyclohexylmethyl, methyl, benzyl, methylsulfinylethyl and N-(methyl)indol-3-ylmethyl;
$R^2$ is selected from the group consisting of cyclohexyl, cyclohexylmethyl, benzyl, hydroxyethyl, 4-methoxybenzyl, 2-methylpropyl and indol-3-ylmethyl; and
$R^3$ is selected from the group consisting of 4-tert-butyl-1-cyclohexylmethyl, 1-adamantylethyl, cyclohexylbutyl, ethyl, 4-biphenylethyl and 2,4-dinitrobenzyl.

7. A single bicyclic guanidine compound of the structure:

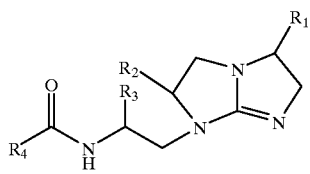

wherein:
$R^1$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, and substituted benzyl;

$R^2$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, and substituted benzyl;

$R^3$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, $C_3$ to $C_7$ substituted cycloalkyl, benzyl, and substituted benzyl; and $R^4$ is selected from the group consisting of a hydrogen atom, $C_1$ to $C_{10}$ alkyl, $C_2$ to $C_{10}$ alkenyl, $C_1$ to $C_{10}$ substituted alkyl, $C_2$ to $C_{10}$ alkynyl, $C_3$ to $C_7$ substituted cycloalkyl, $C_3$ to $C_7$ cycloalkenyl, $C_3$ to $C_7$ substituted cycloalkenyl, $C_7$ to $C_{16}$ phenylalkyl, $C_7$ to $C_{16}$ substituted phenylalkyl, $C_7$ to $C_{16}$ phenylalkenyl and $C_7$ to $C_{16}$ substituted phenylalkenyl, or a pharmaceutically-acceptable salt thereof.

8. The compound of claim 7, wherein either $R_1$ or $R_2$ or both $R_1$ and $R_2$ is not a hydrogen atom.

9. The compound of claim 7, wherein:
$R^1$ is selected from the group consisting of methyl, benzyl, 2-butyl, 2-methylpropyl, 2-propyl, 2-bromobenzyloxycarbonylbenzyl, ethyl, 2-methylpropyl, propyl, butyl, 2-napthylmethyl, cyclohexylmethyl, 4-fluorobenzyl, 4-chlorobenzyl, cyclohexyl, 4-ethoxybenzyl, 4-iodobenzyl, and 4-methoxybenzyl;

$R^2$ is selected from the group consisting of methyl, benzyl, 2-butyl, 2-methylpropyl, 2-propyl, 2-bromobenzyloxycarbonylbenzyl, ethyl, propyl, butyl, 2-naphthylmethyl, methylsulfonylethyl, cyclohexylmethyl, 4-fluorobenzyl, 4-chlorobenzyl, cyclohexyl, 4-ethoxybenzyl, 4-iodobenzyl, and 4-methoxybenzyl;

$R^3$ is selected from the group consisting of methyl, benzyl, hydrogen, 2-methylpropyl, propyl, butyl, cyclohexylmethyl, 4-ethoxybenzyl, and 4-methoxybenzyl; and $R^4$ is selected from the group consisting of 1-phenyl-1-cyclopropyl, 1-phenylpropyl, 2-phenylpropyl, m-xylyl, 3-fluorobenzyl, 3-bromobenzyl, 3-trifluoromethylbenzyl, p-xylyl, 3-methoxybenzyl, 4-bromobenzyl, 4-methoxybenzyl, 4-ethoxybenzyl, 1-(4-isobutylphenyl)ethyl, 3,4-dichlorobenzyl, 3-(3,4-dimethoxy)ethyl, 4-biphenylmethyl, 1-phenylpropen-2-yl, 2-trifluoromethylstryl, 3,4-dimethoxybenzyl, 3,4- dihydroxybenzyl, 2-methoxystyryl, phenyl, 4-chlorostyryl, 3-methoxyphenyl, 4-isopropylphenyl, 4-vinylphenyl, 4-fluorophenyl, 4-bromophenyl, 3,4-dimethoxystyryl, trans-styryl, 3,4-dimethylphenyl, 3-fluoro-4-methylphenyl, 3-bromo-4-methylphenyl, 3-iodo-4-methylphenyl, 3,4-dichlorophenyl, 4-biphenyl, 3,4-difluorophenyl, m-tolyl, benzyl, phenethyl, 3-methoxy-4-methylphenyl, 3-phenylpropyl, 3,4-dimethoxyphenyl, 4-ethyl-4'-biphenyl, 3,4,5-trimethoxyphenyl, propyl, hexyl, 2-propyl, (+/−)-2-butyl, isobutyl, 2-methylbutyl, isovaleryl, p-tolyl, p-anisyl, cyclohexyl, cyclohexylmethyl, cyclohexylpropyl, cycloheptyl, methyl, 2-methylcyclopropyl, cyclobutyl, cyclopentyyl, cyclopentylethyl, 2-furyl, cyclohexylethyl, 4-methylcyclohexyl, 4-t-butylcyclohexyl, 4-methylcyclohexylmethyl, but-2-en-1-yl, 2-norbornylmethyl, and 2-thienyl.

10. The compound of claim 1, wherein:

$R^1$ is selected from the group consisting of methyl, benzyl, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, dimethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, 4-iodobenzyl, 4-methoxybenzyl and N-(methyl)indol-3-ylmethyl;

$R^2$ is selected from the group consisting of methyl, benzyl, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, hydroxyethyl, 4-iodobenzyl, 4-methoxybenzyl and indol-3-ylmethyl; and $R^3$ is selected from the group consisting of 3-phenylbutyl, m-toluylethyl, 3-fluorophenylethyl, p-toluylethyl, 4-fluorophenylethyl, 3-methoxyphenylethyl, 4-methoxyphenylethyl, 4-ethoxyphenylethyl, 3-(3,4-dimethoxyphenyl)propyl, 4-biphenylethyl, 3,4-dimethoxyphenylethyl, phenylethyl, 3-phenylpropyl, 4-phenylbutyl, butyl, heptyl, isobutyryl, (+/−)-2-methylbutyl, isovaleryl, 3-methylvaleryl, 4-methylvaleryl, (tert-butyl)ethyl, cyclohexylmethyl, cyclohexylethyl, cyclohexylbutyl, cycloheptylmethyl, 2-hydroxypropyl, ethyl, cyclobutylmethyl, cyclopentylmethyl, 3-cyclopentylpropyl, cyclohexylpropyl, 4-methyl-1-cyclohexylmethyl, 4-(tert-butyl)-1-cyclohexylmethyl, 2-norbornylethyl, 1-adamantylethyl, 2-ethylbutyl, 3,3-diphenylpropyl, 2-methyl-4-nitro-1-imidazolylpropyl, cyclopentylethyl, 3-indolylethyl and 2,4-dinitrophenylethyl.

11. The compound of claim 1, wherein:

$R^1$ is selected from the group consisting of methyl, benzyl, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, dimethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, 4-iodobenzyl, 4-methoxybenzyl and N-(methyl)indol-3-ylmethyl;

$R^2$ is selected from the group consisting of benzyl, 2-butyl, N-methyl,N-thiocarbonylimidazole-aminobutyl, 2-methylpropyl, methylsulfinylethyl, guanidinopropyl, 2-propyl, 4-hydroxybenzyl, ethyl, propyl, butyl, N-methyl,N-thiocarbonylimidazole-aminopropyl, 2-naphthylmethyl, cyclohexylmethyl, methylsulfonylethyl, 4-nitrobenzyl, 4-chlorobenzyl, 4-fluorobenzyl, N-ethyl,N-thiocarbonylimidazole-aminobutyl, 3-pyridylmethyl, cyclohexyl, tert-butyl, N-methyl,N-thiocarbonylimidazole-4-aminobenzyl, 4-ethoxybenzyl, hydroxyethyl, 4-iodobenzyl, 4-methoxybenzyl and indol-3-ylmethyl; and $R^3$ is selected from the group consisting of 3-phenylbutyl, m-toluylethyl, 3-fluorophenylethyl, p-toluylethyl, 4-fluorophenylethyl, 3-methoxyphenylethyl, 4-methoxyphenylethyl, 4-ethoxyphenylethyl, 3-(3,4-dimethoxyphenyl)propyl, 4-biphenylethyl, 3,4-dimethoxyphenylethyl, phenylethyl, 3-phenylpropyl, 4-phenylbutyl, butyl, heptyl, isobutyryl, (+/−)-2-methylbutyl, isovaleryl, 3-methylvaleryl, 4-methylvaleryl, (tert-butyl)ethyl, cyclohexylmethyl, cyclohexylethyl, cyclohexylbutyl, cycloheptylmethyl, 2-hydroxypropyl, ethyl, cyclobutylmethyl, cyclopentylmethyl, 3-cyclopentylpropyl, cyclohexylpropyl, 4-methyl-1-cyclohexylmethyl, 4-(tert-butyl)-1-cyclohexylmethyl, 2-norbornylethyl, 1-adamantylethyl, 2-ethylbutyl, 3,3-diphenylpropyl, 2-methyl-4-nitro-1-imidazolylpropyl, cyclopentylethyl, 3-indolylethyl and 2,4-dinitrophenylethyl.

* * * * *